(12) United States Patent
Fram

(10) Patent No.: US 10,129,553 B2
(45) Date of Patent: *Nov. 13, 2018

(54) DYNAMIC DIGITAL IMAGE COMPRESSION BASED ON DIGITAL IMAGE CHARACTERISTICS

(71) Applicant: D.R. Systems, Inc., San Diego, CA (US)

(72) Inventor: Evan K. Fram, Paradise Valley, AZ (US)

(73) Assignee: D.R. Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,121

(22) Filed: Sep. 18, 2017

(65) Prior Publication Data
US 2018/0027250 A1  Jan. 25, 2018

Related U.S. Application Data

(63) Continuation of application No. 15/352,092, filed on Nov. 15, 2016, now Pat. No. 9,800,882, which is a
(Continued)

(51) Int. Cl.
*G06K 9/00* (2006.01)
*H04N 19/426* (2014.01)
(Continued)

(52) U.S. Cl.
CPC ......... *H04N 19/426* (2014.11); *A61B 5/7232* (2013.01); *G06F 19/321* (2013.01);
(Continued)

(58) Field of Classification Search
None
See application file for complete search history.

(56) References Cited

U.S. PATENT DOCUMENTS 6,697,525 B1   2/2004  Sadeh
8,630,501 B1   1/2014  Fram
(Continued)

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
(Continued)

*Primary Examiner* — Delomia L Gilliard
(74) *Attorney, Agent, or Firm* — Michael Best & Friedrich LLP

(57) ABSTRACT

Systems and techniques are disclosed for dynamically and automatically selecting an appropriate compression technique and/or compression parameters for digital images in order to reduce or prevent loss of significant information that may negatively impact the utility or usefulness of the digital images. For example, based on various image characteristics associated with a digital image, the system may dynamically compress the image using particular compression techniques and/or by adjusting compression parameters, to maintain significant information of the image. The system may select compression techniques and/or compression parameters based on one or more compression rules, which may be associated with image characteristics, patient characteristics, medical history, etc. Further, the system may, based on the one or more compression rules, compress the image to a maximum degree of compression while maintaining the significant information of the image.

19 Claims, 12 Drawing Sheets

Related U.S. Application Data continuation of application No. 15/136,555, filed on Apr. 22, 2016, now Pat. No. 9,536,324, which is a continuation of application No. 15/072,109, filed on Mar. 16, 2016, now Pat. No. 9,536,045.

(60) Provisional application No. 62/133,738, filed on Mar. 16, 2015.

(51) Int. Cl.

| | | |
|---|---|---|
| H04N 19/182 | (2014.01) | |
| H04N 19/895 | (2014.01) | |
| H04N 19/67 | (2014.01) | |
| H04N 19/157 | (2014.01) | |
| H04N 19/122 | (2014.01) | |
| H04N 19/119 | (2014.01) | |
| H04N 19/103 | (2014.01) | |
| G06F 19/00 | (2018.01) | |
| G06T 7/00 | (2017.01) | |
| H04N 19/65 | (2014.01) | |
| H04N 19/136 | (2014.01) | |
| A61B 5/00 | (2006.01) | |
| H04N 19/154 | (2014.01) | |
| H04N 19/176 | (2014.01) | |
| G06T 9/00 | (2006.01) | |
| H04N 19/124 | (2014.01) | |
| H04N 19/30 | (2014.01) | |
| A61B 5/055 | (2006.01) | |

(52) U.S. Cl.
CPC .......... *G06T 7/0002* (2013.01); *G06T 7/0012* (2013.01); *G06T 7/0014* (2013.01); *G06T 9/00* (2013.01); *H04N 19/103* (2014.11); *H04N 19/119* (2014.11); *H04N 19/122* (2014.11); *H04N 19/136* (2014.11); *H04N 19/154* (2014.11); *H04N 19/157* (2014.11); *H04N 19/176* (2014.11); *H04N 19/182* (2014.11); *H04N 19/65* (2014.11); *H04N 19/67* (2014.11); *H04N 19/895* (2014.11); *A61B 5/055* (2013.01); *G06T 2207/10072* (2013.01); *G06T 2207/10081* (2013.01); *G06T 2207/20004* (2013.01); *G06T 2207/30004* (2013.01); *G06T 2207/30168* (2013.01); *H04N 19/124* (2014.11); *H04N 19/30* (2014.11)

(56) References Cited

U.S. PATENT DOCUMENTS

| | | | |
|---|---|---|---|
| 9,536,045 B1* | 1/2017 | Fram | G06T 9/00 |
| 9,536,324 B1* | 1/2017 | Fram | G06T 9/00 |
| 9,800,882 B2* | 10/2017 | Fram | H04N 19/426 |
| 2002/0001414 A1 | 1/2002 | Sadeh | |
| 2005/0018908 A1* | 1/2005 | Johannesson | H04N 19/60 382/232 |
| 2008/0232699 A1* | 9/2008 | Gering | H04N 19/63 382/232 |
| 2009/0190847 A1* | 7/2009 | Marks | G06T 9/00 382/239 |
| 2010/0074322 A1 | 3/2010 | Terashima | |
| 2012/0201476 A1* | 8/2012 | Carmel | H04N 19/176 382/239 |
| 2013/0010864 A1* | 1/2013 | Teng | H04N 19/176 375/240.12 |
| 2014/0098115 A1* | 4/2014 | Ju | G06T 9/00 345/520 |
| 2014/0146188 A1 | 5/2014 | Ju et al. | |
| 2014/0146874 A1* | 5/2014 | Ju | H04N 5/23229 375/240.02 |
| 2014/0169133 A1 | 6/2014 | Nemeth et al. | |
| 2017/0064319 A1* | 3/2017 | Fram | G06T 9/00 |

OTHER PUBLICATIONS

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions. Accessed on Feb. 9, 2015.

AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.

DR Systems, Dominator™Guide for Reading Physicians, Release 8.2, 546 pages (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.

Fram et al. "Three-Dimensional Display of the Heart, Aorta, Lungs and Airway Using CT." American Roentgen Ray Society. AJR 139:1171-1176, Dec. 1982.

Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.

(56) References Cited

OTHER PUBLICATIONS

Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See The Future, in 12 pages, color brochure, (BRO80809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do, Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages(IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/ultraVISION.pdf, Accessed on Feb. 9, 2015.
VioStream for VitreaView, 2 color page printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Office Action dated Jun. 17, 2016 in U.S. Appl. No. 15/072,109.
Office Action dated Jul. 1, 2016 in U.S. Appl. No. 15/136,555.
Notice of Allowance dated Oct. 6, 2016 in U.S. Appl. No. 15/072,109.
Notice of Allowance dated Oct. 6, 2016 in U.S. Appl. No. 15/136,555.

(56) References Cited

OTHER PUBLICATIONS

Notice of Allowance dated Jun. 30, 2017 in U.S. Appl. No. 15/352,092.
Notice of Allowability from the U.S. Patent and Trademark Office for U.S. Appl. No. 15/072,109 dated Dec. 2, 2016 (2 pages).
Notice of Allowability from the U.S. Patent and Trademark Office for U.S. Appl. No. 15/136,555 dated Dec. 2, 2016 (4 pages).
Notice of Allowance from the U.S. Patent and Trademark Office for U.S. Appl. No. 15/352,092 dated Jun. 30, 2017 (8 pages).
Office Action from the U.S. Patent and Trademark Office for U.S. Appl. No. 15/352,092 dated May 19, 2017 (7 pages).

* cited by examiner

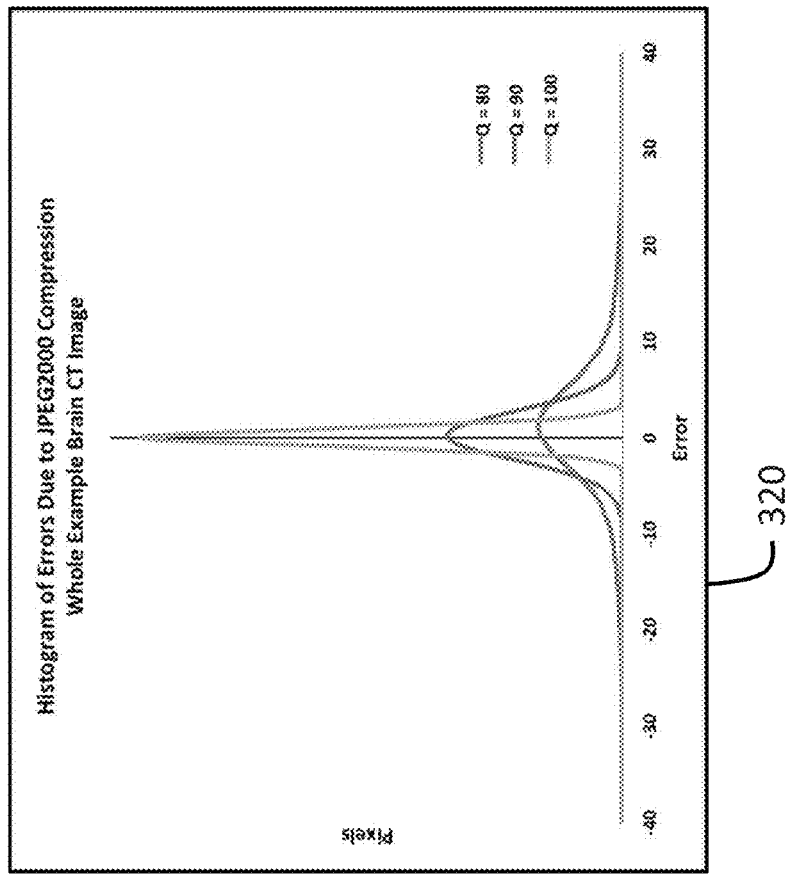
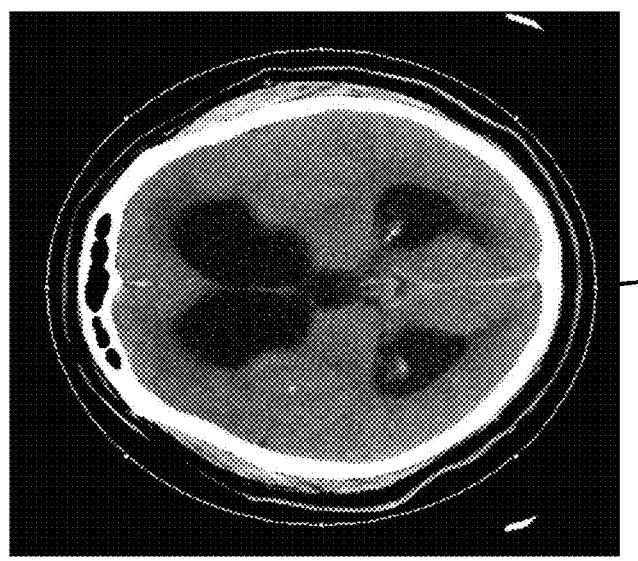
FIG. 3A

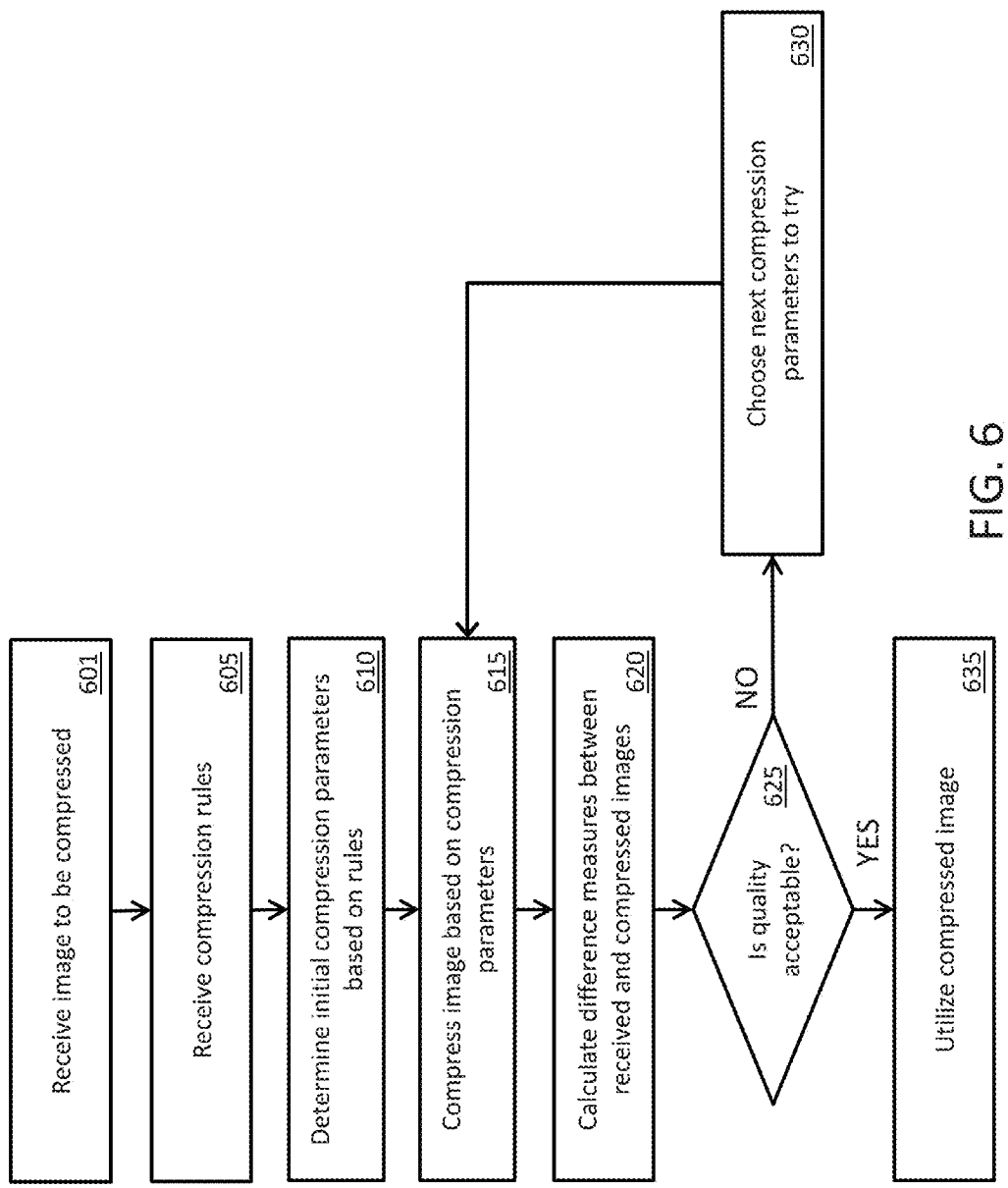

DYNAMIC DIGITAL IMAGE COMPRESSION BASED ON DIGITAL IMAGE CHARACTERISTICS

CROSS-REFERENCE TO RELATED APPLICATIONS

This application is a continuation of U.S. patent application Ser. No. 15/352,092, filed Nov. 15, 2016, and titled "DYNAMIC DIGITAL IMAGE COMPRESSION BASED ON DIGITAL IMAGE CHARACTERISTICS," which is a continuation of U.S. patent application Ser. No. 15/136,555, filed Apr. 22, 2016, and titled "DYNAMIC DIGITAL IMAGE COMPRESSION BASED ON DIGITAL IMAGE CHARACTERISTICS," which is a continuation of U.S. patent application Ser. No. 15/072,109, filed Mar. 16, 2016, and titled "DYNAMIC DIGITAL IMAGE COMPRESSION BASED ON DIGITAL IMAGE CHARACTERISTICS," which application claims benefit of U.S. Provisional Patent Application No. 62/133,738, filed Mar. 16, 2015, and titled "CLINICALLY SAFER MEDICAL IMAGE COMPRESSION BASED ON DYNAMIC SELECTION OF COMPRESSION AND COMPRESSION RULES." The entire disclosure of each of the above items is hereby made part of this specification as if set forth fully herein and incorporated by reference for all purposes, for all that it contains.

Any and all applications for which a foreign or domestic priority claim is identified in the Application Data Sheet as filed with the present application are hereby incorporated by reference under 37 CFR 1.57.

TECHNICAL FIELD

Embodiments of the present disclosure relate to systems and techniques for dynamic image compression based on image contents.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Digital images are generally stored as digital data (also referred to herein as "image data"). For example, bitmapped or pixmapped digital images are represented by arrays of pixel data, where pixels of the digital images are arranged in columns and rows. The pixel data may include ranges of values representing, for example, color and/or intensity values.

Digital images may be compressed. Compression may be desirable to reduce file sizes of, and thus storage space requirements for, the digital images. Compression may be lossless or lossy. In lossless compression, no image data of the digital image is lost. In lossy compression, some of the image data of the digital image is lost.

SUMMARY

The systems, methods, and devices described herein each have several aspects, no single one of which is solely responsible for its desirable attributes. Without limiting the scope of this disclosure, several non-limiting features will now be described briefly.

In some cases, lossy compression is desirable due to a substantial reduction in file size (as compared to lossless compression), even considering the loss of image data of the digital image. However, it may also be desirable to ensure that the amount of, and/or type of, image data lost does not negatively impact the utility or usefulness of the digital image.

For example, in certain applications lossy compression of digital images may be desirable due to the large amount of image data of each digital image, and in view of storage and/or bandwidth requirements (e.g., transfer of uncompressed digital images from one place to another may be very time consuming or expensive, storage of uncompressed digital images may be expensive or unfeasible, and/or decoding and/or rendering of uncompressed digital images may be time consuming and/or use significant processing power). However, in these applications it may also be important that "significant information" of the digital images is not lost as a result of the lossy compression. What constitutes "significant information" of any given digital image may vary depending on a field of application of the digital image, a context of the digital image, and/or the like.

For example, in the context of medical imaging, some loss of visual information may be acceptable, but the lost visual information should not include "clinically significant information." For example, a digital image may include clinically significant information including indications of cancer cells in the tissue of a patient. In this case, compression of the digital image should not remove or obscure the indications of cancer cells. Otherwise, the usefulness of the digital image (e.g., visually indicating cancer cells to someone reading the digital image) would be lost as a result of the compression.

Studies of lossy compression of digital images in the medical imaging context may involve radiologists viewing a finite set of digital images to determine whether or not there is a perceptible difference between the original and compressed versions of each digital image. Conclusions regarding the type and degree of compression are then used by hospitals and imaging centers to set the degree and type of image compression used routinely. Such conclusions drawn from these relatively small studies are often then applied routinely to large sets of digital image data, for example, to the over one billion radiology exams performed each year in the US alone.

There are several potential problems with previous approaches to digital image compression in the medical imaging field. First, conclusions drawn from studies of relatively small numbers of digital images may not apply to all digital images in the clinical environment, where there may be a much wider range of image variation, e.g. related to technical parameters and pathology. For example, a compression technique that generally works well for a test group of digital images (e.g., provides no loss in clinically significant information in compressed image data), might not work well on a particular digital image of one patient's medical imaging exam and result in a misdiagnosis in that patient. In addition, compression recommendations based on even a signal modality, such as CT, might not be reasonable when CT parameters and technology evolves over time. For example, it has been demonstrated that compression tolerance is lower for thinner CT images.

Second, for some modalities clinical decisions are based on quantitative measurements (e.g., by electronic analysis) of digital image characteristics. For example, pixel/signal intensity, that may not be visually perceptible to radiologists viewing images, may be electronically analyzed to determine clinical decisions. For example, in CT the signal intensity of pixels (also referred to herein as "pixel intensity") in digital images may be represented in Hounsfield Units (HU), where water has 0 HU and air −1,000 HU. Most soft tissues have HU values above 0, with the exception of fat. In some clinical scenarios, measurement of pixel/signal intensity is used as part of the clinical assessment of a lesion. For example, in the assessment of renal and adrenal masses, measurement of a lesion's pixel/signal intensity is used as one of the factors to determine if the mass is likely to be benign or potentially malignant. Compression of a CT image could result in subtle changes in image pixel/signal intensity that might not be visually apparent, but could result in a small change in pixel/signal intensity that, when measured, results in a misdiagnosis. Other examples where quantitative measurement of image pixel/signal intensity is used for clinical diagnosis include dynamic breast MRI used for assessment of breast masses and measurement of SUV in PET imaging.

And third, there may be variations in the way compression techniques (e.g., lossy compression techniques) are implemented. Generally, a degree of compression can be set in two ways: (1) by setting a Compression Ratio (CR), and/or (2) by setting a Quality Factor. In some instance, setting a fixed Compression Ratio is a problem in that loss of quality depends on technical factors, including noise and digital image complexity. While setting a constant Quality Factor could in theory mitigate these issues, there is no standard across vendors for how Quality Factor is implemented.

Accordingly, current techniques for compressing digital images, in certain fields of application, may be inadequate because significant information in the image data may be inadvertently lost. In the context of medical imaging, this could potentially be dangerous, such as if lost information results in misdiagnoses. Therefore, a more effective and safer method of selecting digital image compression techniques and parameters is needed.

Embodiments of the present disclosure relate to systems and techniques for dynamically selecting an appropriate compression technique and/or compression parameters for digital images in order to reduce or prevent loss of significant information that may negatively impact the utility or usefulness of the digital images. For example, based on various image characteristics associated with a digital image, the system may dynamically compress the image using particular compression techniques and/or by adjusting compression parameters, to maintain significant information of the image. The system may select compression techniques and/or compression parameters based on one or more compression rules, which may be associated with image characteristics, patient characteristics, medical history, etc. Further, the system may, based on the one or more compression rules, compress the image to a maximum degree of compression while maintaining the significant information of the image. If an acceptable compression cannot be achieved (e.g., using any available lossy compression technique) while maintaining the significant information of the image, the system may compress the image using a lossless compression technique.

In some implementations, images may be segmented such that different compression (where a "compression" generally includes a compression technique and compression parameters for use with the compression technique) may be applied to different portions of the images. For example, portions of an image including significant information may be may be compressed less than portions of an image without significant information.

In the context of medical imaging, the system may process a patient's medical exam such that images of the exam are automatically compressed based on one or more characteristics associated with the images (including, for example, characteristics of the exam and/or image series of the exam) and one or more compression rules, such that certain significant information is not lost from the images.

Accordingly, in various embodiments, large amounts of data are automatically and dynamically calculated interactively in response to user inputs, and the calculated data (e.g., image data) may be efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additionally, it has been noted that the design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The present disclosure describes various embodiments of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, image data (including digital images) and may enable a user to more quickly and accurately access, navigate, assess, and digest the image data than previous systems.

Further, the interactive and dynamic user interfaces described herein are enabled by innovations in efficient interactions between the user interfaces and underlying systems and components. For example, disclosed herein are improved methods of receiving user inputs (including methods of interacting with, and selecting, images), translation and delivery of those inputs to various system components, automatic and dynamic execution of complex processes in response to the input delivery, automatic interaction among various components and processes of the system, and automatic and dynamic updating of the user interfaces (to, for example, display the relevant digital images). The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing medical image interaction technology (including, e.g., Picture Archiving and Communication Systems ("PACS"), Electronic Medical Record ("EMR") Systems, and/or the like) is limited in various ways (e.g., image compression can remove significant information, image review is slow and cumbersome, comparison of images is inefficient, etc.), and various embodiments of the disclosure provide significant improvements over such technology.

Additionally, various embodiments of the present disclosure are inextricably tied to computer technology. In particular, various embodiments rely on detection of user inputs via graphical user interfaces, calculation of updates to displayed electronic data based on those user inputs, automatic processing of related digital images, efficient compression of digital images, and presentation of the updates to displayed digital images via interactive graphical user interfaces. Such features and others are intimately tied to, and enabled by, computer technology, and would not exist except for computer technology. For example, the compression of digital images and interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic image data, and efficient compression of image data.

According to an embodiment, a method of digital image compression is disclosed comprising: causing execution of software instructions by one or more hardware computing devices in order to: receive an uncompressed digital image; determine a characteristic associated with the uncompressed digital image; access a compression rule associated with the characteristic; compress, based on the compression rule, the uncompressed digital image to generate a first compressed digital image; determine a first amount of errors based on comparison of the first compressed digital image to the uncompressed digital image; compare the first amount of errors to an error threshold included in the compression rule; in response to determining that the first amount of errors exceeds the error threshold, recompress, based on the compression rule, the uncompressed digital image to generate a second compressed digital image having a level of compression less than the first compressed digital image; and determine a second amount of errors based on comparison of the second compressed digital image to the uncompressed digital image.

According to an aspect, the characteristic associated with the uncompressed digital image includes at least one of: an imaging modality, an anatomical feature, or an acquisition type.

According to another aspect, the compression rule indicates a compression algorithm and a first quality factor, and the first compressed digital image is generated based on the compression algorithm and the first quality factor.

According to yet another aspect, the compression rule indicates a second quality factor that is greater than the first quality factor, and the second compressed digital image is generated based on the compression algorithm and a second quality factor.

According to another aspect, determining the first amount of errors comprises: causing execution of software instructions by one or more hardware computing devices in order to: determine a difference between the uncompressed digital image and the first compressed digital image to generate difference image data; and determine the first amount of errors by at least one of: determining a number of pixels in the difference image data having a value indicative of an error, or determining a degree of error in one or more pixels of the difference image data.

According to yet another aspect, determining the first amount of errors comprises: causing execution of software instructions by one or more hardware computing devices in order to: identify one or more pixels of the uncompressed digital image having an intensity value satisfying a threshold; for each pixel of the one or more pixels, determine a difference between the pixel of the uncompressed digital image and the pixel of the first compressed digital image to generate difference image data; and determine the first amount of errors by at least one of: determining a number of pixels in the difference image data having a value indicative of an error, or determining a degree of error in one or more pixels of the difference image data.

According to another aspect, each of the one or more pixels comprises a group of pixels, and wherein each group of pixels comprises at least one of: a 4×4 group of pixels, or a 6×6 group of pixels.

According to yet another aspect, determining the first amount of errors comprises: causing execution of software instructions by one or more hardware computing devices in order to: identify one or more regions of the uncompressed digital image having pixel intensity values satisfying a threshold; for each pixel or group of pixels of the one or more regions, determine a difference between the pixel of the uncompressed digital image and the pixel of the first compressed digital image to generate difference image data; and determine the first amount of errors by at least one of: determining a number of pixels in the difference image data having a value indicative of an error, or determining a degree of error in one or more pixels of the difference image data.

According to another aspect, the method further comprises: causing execution of software instructions by one or more hardware computing devices in order to: store the second compressed digital image in a data store.

According to yet another aspect, the method further comprises: causing execution of software instructions by one or more hardware computing devices in order to: in response to determining that the second amount of errors exceeds the error threshold defined by the compression rule, recompress the uncompressed digital image using a lossless compression technique to generate a third compressed digital image; and store the third compressed digital image in a data store.

According to another embodiment, a method of digital image compression is disclosed comprising: causing execution of software instructions by one or more hardware computing devices in order to: receive an uncompressed digital image; determine a characteristic associated with the uncompressed digital image; access a compression rule associated with the characteristic; compress, based on the compression rule, the uncompressed digital image using each of a plurality of compression levels to generate a set of compressed digital images that are each compressed at different compression levels; for each of the compressed digital images of the set, determine a respective amount of errors based on comparison of the respective compressed digital images to the uncompressed digital image; and determine a first compressed digital image of the set that: is associated with an amount of errors that satisfies a threshold defined by the compression rule, and is compressed at a highest compression level of the plurality of compression levels that has an amount of errors that satisfies the threshold defined by the compression rule.

According to an aspect, the characteristic associated with the uncompressed digital image includes at least one of: an imaging modality, an anatomical feature, or an acquisition type.

According to another aspect, the plurality of compression levels each includes a compression algorithm and a set of respective quality factors, and the set of compressed digital images is generated based on the respective compression algorithms and quality factors.

According to yet another aspect, determining an amount of errors by comparison of a compressed digital image to the uncompressed digital image comprises: causing execution of software instructions by one or more hardware computing devices in order to: determine a difference between the uncompressed digital image and the compressed digital image to generate difference image data; and determine the amount of errors by at least one of: determining a number of pixels in the difference image data having a value indicative of an error, or determining a degree of error in one or more pixels of the difference image data.

According to another aspect, determining an amount of errors by comparison of a compressed digital image to the uncompressed digital image comprises: causing execution of software instructions by one or more hardware computing devices in order to: identify one or more pixels of the uncompressed digital image having an intensity value satisfying a threshold; for each pixel of the one or more pixels, determine a difference between the pixel of the uncompressed digital image and the pixel of the compressed digital image to generate difference image data; determine the amount of errors by at least one of: determining a number of pixels in the difference image data having a value indicative of an error, or determining a degree of error in one or more pixels of the difference image data.

According to yet another aspect, each of the one or more pixels comprises a group of pixels, and wherein each group of pixels comprises at least one of: a 4×4 group of pixels, or a 6×6 group of pixels.

According to another aspect, determining an amount of errors by comparison of a compressed digital image to the uncompressed digital image comprises: causing execution of software instructions by one or more hardware computing devices in order to: identify one or more regions of the uncompressed digital image having pixel intensity values satisfying a threshold; for each pixel or group of pixels of the one or more regions, determine a difference between the pixel of the uncompressed digital image and the pixel of the compressed digital image to generate difference image data; and determine the amount of errors by at least one of: determining a number of pixels in the difference image data having a value indicative of an error, or determining a degree of error in one or more pixels of the difference image data.

According to yet another aspect, the method further comprises: causing execution of software instructions by one or more hardware computing devices in order to: store the first compressed digital image in a data store.

According to another aspect, the method further comprises: causing execution of software instructions by one or more hardware computing devices in order to: in response to determining that none of the compressed digital images of the set is associated with an amount of errors that satisfies the threshold defined by the compression rule, recompress the uncompressed digital image using a lossless compression technique to generate a second compressed digital image; and store the second compressed digital image in a data store.

According to yet another aspect, the highest compression level is a compression level that requires a least amount of storage space as compared to other compression levels of the plurality of compression levels, while having the amount of errors that satisfies the threshold defined by the compression rule.

According to yet another embodiment, a method of digital image compression is disclosed comprising: causing execution of software instructions by one or more hardware computing devices in order to: receive an uncompressed digital image; determine a characteristic associated with the uncompressed digital image; access a compression rule associated with the characteristic; compress, based on the compression rule, the uncompressed digital image using each of a plurality of compression levels to generate a set of compressed digital images that are each compressed at different compression levels; generate, based on the compression rule, a respective correction image for each of the compressed digital images of the set, wherein the correction images, when combined with their respective compressed digital images, removes errors from at least a portion of the respective compressed digital images; and determine a combination of a first compressed digital image and an associated first correction image of the set that requires a minimum amount of storage space.

According to an aspect, the characteristic associated with the uncompressed digital image includes at least one of: an imaging modality, an anatomical feature, or an acquisition type.

According to another aspect, the plurality of compression levels each includes a compression algorithms and a set of respective quality factors, and the set of compressed digital images is generated based on the respective compression algorithms and quality factors.

According to yet another aspect, the method further comprises: causing execution of software instructions by one or more hardware computing devices in order to: identify one or more regions of the uncompressed digital image having pixel intensity values satisfying a threshold; and designate the one or more regions as the portion.

According to another aspect, the one or more regions are identified based on one or more segmentation rules.

According to yet another aspect, the method further comprises: causing execution of software instructions by one or more hardware computing devices in order to: losslessly compress the first associated correction image.

According to another aspect, the method further comprises: causing execution of software instructions by one or more hardware computing devices in order to: store or transmit the combination of the first compressed digital image and the associated first correction image that is losslessly compressed.

According to yet another aspect, the method further comprises: causing execution of software instructions by one or more hardware computing devices in order to: combine the first compressed digital image and the first associated correction image into a single compressed digital image.

According to another aspect, the correction images, when combined with their respective compressed digital images, removes all errors from the respective compressed digital images and results in the uncompressed digital image.

Additional embodiments of the disclosure are described below in reference to the appended claims, which may serve as an additional summary of the disclosure.

In various embodiments, computer systems are disclosed that comprise one or more hardware computer processors in communication with one or more non-transitory computer readable storage devices, wherein the one or more hardware computer processors are configured to execute the plurality of computer executable instructions in order to cause the computer system to perform operations comprising one or more aspects of the above-described embodiments (including one or more aspects of the appended claims).

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, non-transitory computer-readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIGS. 3A-3B are diagrams illustrating various aspects of various example compressed versions of an example digital image, according to an embodiment of the present disclosure;

FIGS. 6-8 are flowcharts illustrating example methods of compressing digital images, according to various embodiments of the present disclosure.

DETAILED DESCRIPTION

Figure 1:
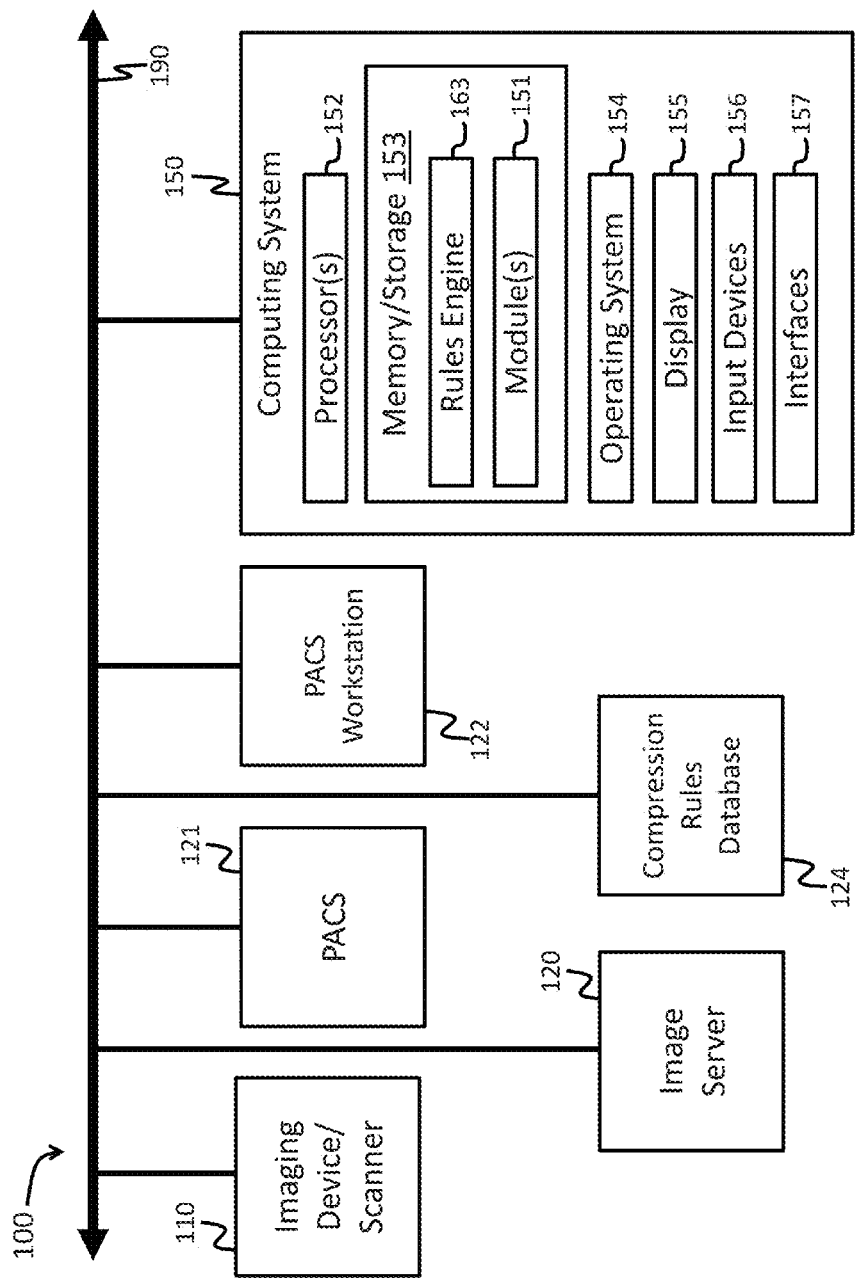
FIG. 1 is a block diagram showing various aspects of a computing system and network environment in which the computing system may be implemented, according to various embodiments of the present disclosure.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

I. Overview

As mentioned above, current techniques for compressing digital images, in certain fields of application, may be inadequate because significant information in the image data may be inadvertently lost. In the context of medical imaging, this could potentially be dangerous and result in misdiagnoses. Systems and techniques of the present disclosure overcome certain problems with the current techniques.

In particular, embodiments of the present disclosure relate to systems and techniques for dynamically and automatically selecting an appropriate compression technique and/or compression parameters for digital images in order to reduce or prevent loss of significant information that may negatively impact the utility or usefulness of the digital images. For example, based on various image characteristics associated with a digital image, the system may dynamically compress the image using particular compression techniques and/or by adjusting compression parameters, to maintain significant information of the image. The system may select compression techniques and/or compression parameters based on one or more compression rules, which may be associated with image characteristics, patient characteristics, medical history, etc. Further, the system may, based on the one or more compression rules, compress the image to a maximum degree of compression while maintaining the significant information of the image. If an acceptable compression cannot be achieved (e.g., using any available lossy compression technique) while maintaining the significant information of the image, the system may compress the image using a lossless compression technique.

In some implementations, images may be segmented such that different compression (where a "compression" generally includes a compression technique and compression parameters for use with the compression technique) may be applied to different portions of the images. For example, portions of an image including significant information may be compressed less than portions of an image without significant information.

In the context of medical imaging, the system may process a patient's medical exam such that images of the exam are automatically compressed based on one or more characteristics associated with the images (including, for example, characteristics of the exam and/or image series of the exam) and one or more compression rules, such that certain significant information is not lost from the images.

In the context of medical imaging, examples of image characteristics based upon which compression rules may be selected include:

Modality. For example, for CT images, compression rules may take into account strict requirements with regard to change in pixel/signal intensity (because, for example, significant information for CT images may include quantitative signal intensity measurements). In another example, for chest radiography, compression rules may take into account that pixel/signal intensity is arbitrary and not used for quantitative measurement (and thus, signal intensity is not part of the significant information of chest radiography images).

Acquisition type within a modality. For example, for breast MRI images, compression rules may take into account that, for some image series (e.g. dynamic enhanced series) relative changes in pixel/signal intensity may be important (e.g., include significant information), while for other image series (e.g., anatomic series) pixel/signal intensity is not as important (e.g., other visual assessment information is significant information).

Whether or not images are to be combined into a multi-planar reformatted images or 3D volumetric images. For example, in these cases the compression rules may take into account that it might be important that the same compression parameters be applied to every image in a series.

In some implementations, compression rules may further be selected based on other characteristics, such as patient characteristic, medical history of a patient, user characteristics, etc. For example, certain compression rules may be associated with particular users, groups of users, sites, etc., such that different compression rules may be applied depending on who is viewing the images and/or where the images are being viewed. For example, on user may prefer less compressed images than another user, thus the user may specify a particular set of compression rules that are specific to that user.

Accordingly, in some cases, in the context of medical imaging, the system, based on the compression rules, may select a single compression technique (e.g., compression algorithm and associated compression parameters) to apply to all images in a series of a medical exam. For example, a lowest degree of compression required for any image in a series or exam (e.g., a degree of compression that ensures that all images in the series or exam maintain significant information) may be tested against all images in the series or exam to ensure that all images pass a quality assessment (e.g., that significant information is retained in all images of the series or exam). If one or more images fail the quality assessment, then other compression settings may be tried until one is found that allows all the images in the series or exam to pass the quality assessment.

While systems and techniques of the present disclosure are described and illustrated in the context of medical imaging, these systems and techniques may be applied to various other fields of application. For example, the systems and techniques may be applied in the fields of aircraft failure detection, law enforcement, semiconductor fabrication, and/or the like. Further, the systems and techniques may be applied to other types of data other than digital images. For example, the systems and techniques may be applied to compression of video data, sound data, text/file data, and/or the like.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

II. Terms

In order to facilitate an understanding of the systems and methods discussed herein, a number of terms are defined below. The terms defined below, as well as other terms used herein, should be construed broadly to include the provided definitions, the ordinary and customary meaning of the terms, and/or any other implied meaning for the respective terms. Thus, the definitions below do not limit the meaning of these terms, but only provide exemplary definitions.

User: Also referred to herein as "reviewer" and/or "viewer." An individual (or group of individuals) that interfaces with a computing device to, for example, view digital images. In the context of medical imaging, users may include, for example, physicians (including, for example, doctors, radiologists, etc.), hospital staff, and/or any other individuals (including persons not medically trained) involved in viewing, analysis, annotation, comparison, acquisition, storage, management, or other tasks related to digital images as described herein.

User Input (also referred to as "Input"): As used herein in reference to user interactions with data displayed by a computing system, "user input" is a broad term that refers to any type of input provided by a user that is intended to be received and/or stored by the system, to cause an update to data that is displayed by the system, and/or to cause an update to the way that data is displayed by the system. Non-limiting examples of such user input include keyboard inputs, mouse inputs, digital pen inputs, voice inputs, finger touch inputs (e.g., via touch sensitive display), gesture inputs (e.g., hand movements, finger movements, arm movements, movements of any other appendage, and/or body movements), and/or the like. Additionally, user inputs to the system may include inputs via tools and/or other objects manipulated by the user. For example, the user may move an object, such as a surgical instrument, tool, stylus, or wand, to provide inputs. Further, user inputs may include motion, position, rotation, angle, alignment, orientation, configuration (e.g., fist, hand flat, one finger extended, etc.), and/or the like. For example, user inputs may comprise a position, orientation, and/or motion of a hand and/or a 3D mouse.

Digital Image (also referred to as an "Image"): Any collection of digital data (also referred to herein as "image data") that may be rendered visually. Digital images may be acquired via various methods, including by images sensors (such as CCD, CMOS, NMOS, etc.), microscopy (e.g., optical, scanning probe, electron, etc.), optical coherence tomography (OCT), radiography (e.g., x-ray), computed tomography (CT), magnetic resonance imaging (MRI), Ultrasound (US), positron emission tomography scan (PET), nuclear scan (NM), etc. In the context of medical imaging, digital images may include, for example, any type of digital image of an organism (e.g., a human patient). Common types of digital images in the field of medical imaging include but are not limited to radiograph images (e.g., an x-ray image), computed tomography (CT) images, magnetic resonance imaging (MRI) images, Ultrasound (US) images, mammogram images, positron emission tomography scan (PET) images, nuclear scan (NM) images, pathology images, endoscopy images, ophthalmology images, or many other types of digital images. Digital images, particularly in medical imaging, may be reconstructed and/or rendered from 3D or volumetric image data using methods including multiplanar reformation/reconstruction (MPR), maximum intensity projection (MIP), and/or the like (including, e.g., any Computerized Advanced Processing (CAP), as described below).

Compressed Digital Image (also referred to as a "Compressed Image"): A digital image that has been compressed via either a lossless or a lossy compression technique (e.g., a compression algorithm) into a compressed format. Examples of common compression formats include BMP, TIFF, JPEG, GIF, and PNG. Any given compression technique may include one or more "compression parameters" that may affect an amount of, or type of, compression that is applied by the compression technique. As described below, one compression parameter than may be applicable to certain compression techniques is a "quality factor".

Modality: A medical imaging method (e.g., a patient who undergoes an MRI is said to have been scanned with the MRI modality).

Digital Image Series (also referred to as a "Series"): Any two or more digital images that are related. Digital images in a series typically share one or more common characteristics. For example, in the context of medical imaging, such common characteristics may include a type of anatomic plane and/or an image orientation. For example, a digital image series may comprise two or more digital images of a particular patient that are acquired on a particular date, e.g., different x-ray projections of the chest. A series of contiguous 3 mm axial CT scans of the chest is another example of a digital image series. A brain MRI scan might include the following series: sagittal T1 weighted images, axial T1 weighted images, axial FLAIR images, axial T2 weighted images, as well as post contrast axial, sagittal and coronal T1 weighted series.

Medical Imaging Exam (also referred to as a "Medical Exam" and/or an "Exam"): A collection of data related to an examination of a patient. May be specific to a particular time or time period. Generally includes one or more digital images and/or image series, reports, notes, graphs, measurements, annotations, videos, sounds or voice data, diagnoses, and/or other related information. May include multiple image series of multiple modalities, volumetric imaging data, reconstructed images and/or rendered images. For example, an exam of a patient may be the brain MRI scan mentioned above, and may include each of the image series obtained on a particular date including: sagittal T1 weighted images, axial T1 weighted images, axial FLAIR images, axial T2 weighted images, as well as post contrast axial, sagittal and coronal T1 weighted series. Another example of an exam may be a dual-energy radiography exam, which may include image data including traditional x-ray image images, bone subtracted (or "bone out") x-ray images, and/or tissue subtracted (or "tissue out") x-ray images.

Significant Information: Any information conveyed by a digital image that is relevant to the utility or usefulness of the digital image. What constitutes "significant information" of any given digital image may vary depending on one or more "image characteristics" of the digital image. In the context of medical imaging, "significant information" may also be referred to as "clinically significant information" as the significant information may relate, e.g., to clinical diagnoses of a patient. For example, a digital image may include clinically significant information including indications of cancer cells in the tissue of a patient. In some instances significant information may be detected visually, e.g., may be viewable by a user when the image is visually rendered. In other instances, significant information may be detected by analysis of image data (including, e.g., by any Computerized Advanced Processing (CAP), as described below). For example, image pixel intensity values may be analyzed to determine clinically significant information, as mentioned above.

Image Characteristic: Any characteristic related to a digital image. Image characteristics may include, for example, a field of application of the digital image (e.g., medical imaging, aircraft failure detection, law enforcement, semiconductor fabrication, etc.), a type of (or method of acquisition of) the digital image (e.g., CT scan, OCT, CCD, etc.), a context of the digital image (e.g., patient diagnosis, airplane wing analysis, license plate reading, face detection, chip analysis, satellite image, etc.), content of the digital image (e.g., CT scan of brain, portion of airplane wing, license plate, face, chip transistors, terrain, etc.), features of interest in the digital image (e.g., cancer cells, microfractures in metal, license plate numbers/letters, facial features, transistor defects, roads, etc.), a user/group/site/etc. that may view the digital image or where the digital image may be viewed, and/or the like. Additional examples of image characteristics that may be relevant to the medical imaging context include, for example, image modality (e.g., CT, MRI, radiography, etc.), acquisition type (e.g., dynamic enhanced MRI, anatomic MRI, etc.), image angle (e.g., an angle of an image with reference to a standard one or more planes of human anatomy; also referred to herein as "scan plane"), anatomical position (and/or location) (e.g., a location, with reference to a standard one or more planes of human anatomy, of the patient represented in a particular image), image orientation (e.g., an orientation of the image with reference to a standard one or more planes of human anatomy), image rotation (e.g., a rotation of the image with reference to a standard one or more planes of human anatomy), image field of view, slice thickness, image window and/or level (e.g., a contrast of the image, a brightness of the image, and/or the like), image color map (e.g., that includes information for rendering different pixel intensities as different colors), other color characteristics, image opacity (and/or opacity map), image zoom level, image cropping information, and/or the like. In some instances, image characteristics may further include characteristics associated with a series or exam (e.g., clinical indication, patient characteristics, etc.). In some instances, image characteristics may include information about intended processing of the image. For example, the image characteristics may include information about whether or not images are to be combined into a multiplanar reformatted images or 3D volumetric images. In some instances, one or more image characteristics may be user defined and/or based on user preferences (and/or group/site preferences). These image characteristics are provided for illustrative purposes only, as such (and other) characteristics may be grouped, separated, and/or combined differently than described above.

Computerized Advanced Processing (CAP): Any computerized analysis, analysis technique, and/or processing technique discussed herein, and/or any similar computerized processing technique that is currently or later available. CAP and the systems and methods described herein may be applied in various areas including, but not limited to, various types of captured digital images (for example, in the context of medical imaging: cardiology, dermatology, pathology and/or endoscopy, among others; in other contexts: surveillance imaging, satellite imaging, and the like), computer generated digital images (for example, in the context of medical imaging: 3D images from virtual colonoscopy, 3D images of vessels from CTA, and the like), as well as non-imaging data including audio, text, and numeric data. In some embodiments, CAP may include, but is not limited to, significant information detection, image feature detection, image segmentation, pixel intensity analysis, volume rendering (including, for example, multiplanar reformation/reconstruction (MPR), maximum intensity projection (MIP), 3D volume rendering, and/or 3D surface rendering), graphical processing/reporting (e.g., automated identification and outlining of lesions, lumbar discs etc.), automated measurement of lesions or other anatomical features, other image processing techniques, and/or the like.

III. Example Computing Devices and Systems

FIG. 1 is a block diagram showing various aspects of a computing system 150 and network environment 100 in which the compression computing system 150 may be implemented, according to various embodiments of the present disclosure. The compression computing system 150 may be referred to herein as the "computing system," the "system," and/or the like.

As shown, the network environment 100 may include the computing system 150, a computer network 190, an image server 120, a compression rules database 124, a rules engine 163, one or more imaging devices or scanners 110, a Picture Archive and Communication System (PACS) 121, and/or a PACS Workstation 122.

As described below, in various embodiments the computing system 150, the image server 120, the compression rules database 124, the rules engine 163, the one or more imaging devices or scanners 110, the Picture Archive and Communication System (PACS) 121, and/or the PACS Workstation 122 may be in communication with one another via the computer network 190. In some embodiments, various of the image server 120, the compression rules database 124, the rules engine 163, the one or more imaging devices or scanners 110, the Picture Archive and Communication System (PACS) 121, and/or the PACS Workstation 122 may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

The computing system 150 may include various components as shown and described in detail below. As described below, the computing system 150 may display digital images (including, e.g., medical images) and/or other data to a user via a display 155. The computing system 150 may include one or more input devices 156 that detect input from a user as described below. As described below, the computing system 150 may display user interfaces, digital images, and/or the like, to a user via a display 155. Further, user input may be received via the computing system 150, for example selection of exams, images, compressions parameters and/or the like, in response to which the information displayed may be updated.

Additional components of the computing system 150 may include, for example, one or more processors 152 and memory and/or data storage 153 (including one or more software modules 151 and/or a rules engine 163 (which may itself comprise a software module)). In particular, as described below, the rules engine 163 may execute various rules (for example, one or more rules stored in the compression rules database 124) that may be used to compress digital images based on compression rules and image characteristics, translate various user inputs into corresponding changes of displayed images and/or other data, and/or the like.

"Compression rules" are described above and below, and include any rules of the compression rules database 124 that may be executed by the rules engine 163 to determine compression of data, including image data. Compression rules may be associated with one or more image characteristics, for example, to indicate compression techniques and/or compression parameters, among other aspects as described herein. Further, as described above, compression rules may be associated with particular users, user groups, sites, etc. Examples of compression rules are described below in references to FIGS. 5A-5C.

"Segmentation rules" are described below, and include any rules of the system that may be executed by the rules engine 163 to determine segmentation of data, including image data. Segmentation rules may be associated with image characteristics, for example, to determine particular portions of an image to be compressed differently, among other aspects as described herein. Further, segmentation rules may be associated with particular users, user groups, sites, etc. (as described herein). Examples of segmentation rules are described below in references to FIG. 4.

In various embodiments, any of the rules of the compression rules database 124 (including, e.g., compression rules) may be selected based on, for example, one or more image characteristics of image data and/or an identifier or characteristic associated with a user. In various embodiments, any rules and/or particular sets of rules of the compression rules database 124 may be associated with specific users, groups of users (e.g., a type of doctor, etc.), sites (e.g., a hospital, etc.), other characteristics of users, computing devices used the users, and/or the like. Thus, rules may be automatically selected by the system based on one or more characteristics associated with a user. In some embodiments, a default set of rules may apply to all user interactions, and/or when there are no rules specifically associated with the user. The various rules may be provided by the users themselves, by a system administrator, and/or they may be preprogrammed in to the system.

As further described below, network environment 100 may include a server 120 that provides information that is displayed by computing system 150. The server 120 may also include image storage (for example, a data store, database, and/or storage system) that may be configured to store information, such as image data, that is processed by server 120 and/or computing system 150. In various embodiments, image data is stored in Digital Imaging and Communications in Medicine ("DICOM") format and/or any other appropriate format.

The one or more imaging devices/scanners 110 may acquire image data (e.g., digital images, medical imaging data, digital image series, etc.) to be processed by the system and displayed to a user. Imaging devices/scanners 110 may include scanners of a variety of technologies, for example, computed tomography (CT), magnetic resonance imaging (MRI), ultrasounds, nuclear medicine, positron emission computed tomography (PET), radiography, mammography, and/or the like. Additional examples and details of the imaging devices/scanners 110 are described above below.

The network environment 100 also includes the PACS 121 that may be used to manage medical imaging exams, as described in further detail below.

IV. Examples of Digital Image Compression and Analysis

Figure 2:
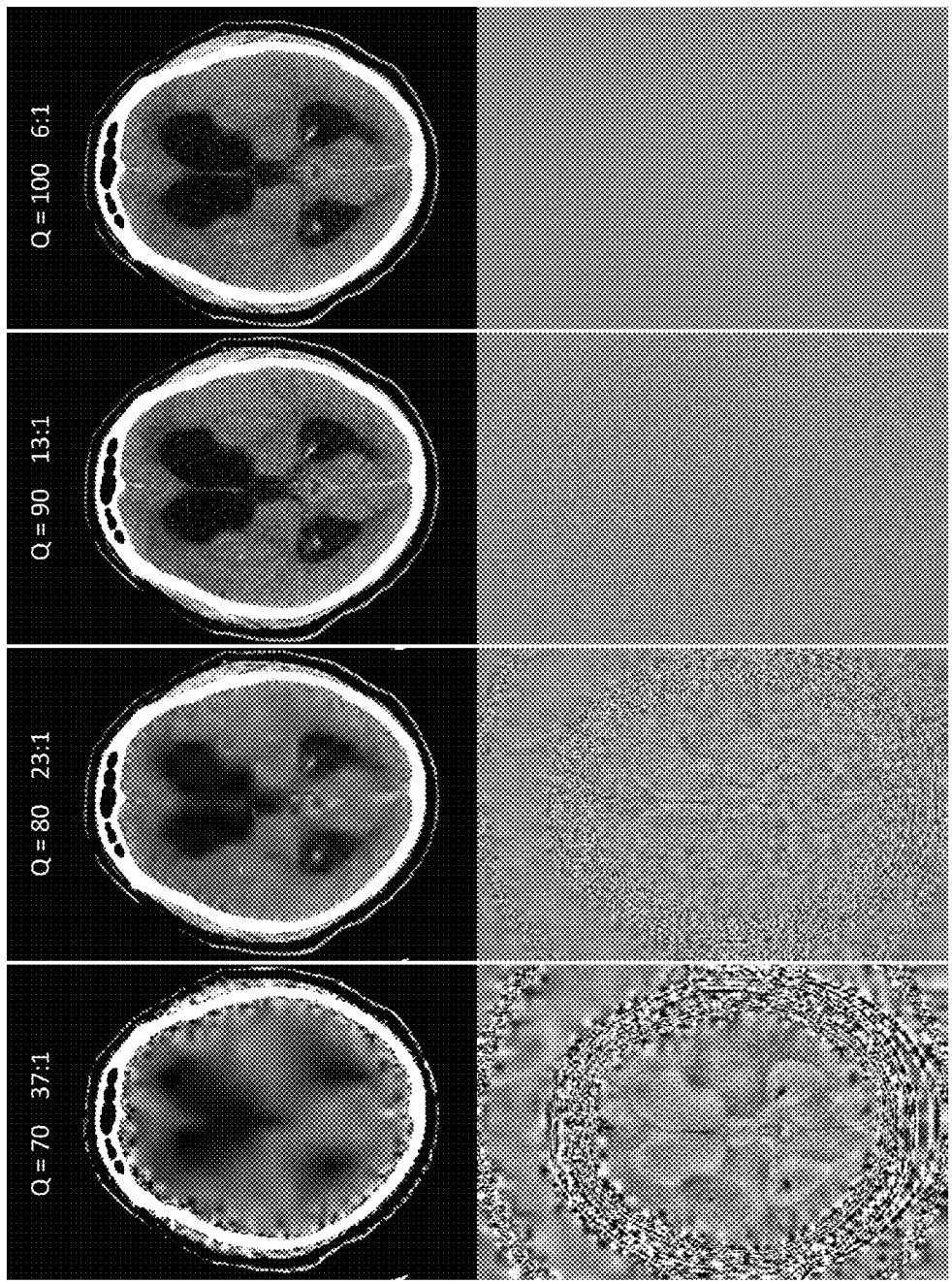
FIG. 2 is a diagram illustrating various example compressed versions of an example digital image, according to an embodiment of the present disclosure.

FIG. 2 is a diagram illustrating various example compressed versions of an example digital image, according to an embodiment of the present disclosure. As shown, FIG. 2 includes two rows, each containing four images. The first row displays compressed versions of an original image 310 of FIG. 3. The images are compressed with a lossy JPEG 2000 compression algorithm using four different quality factors (which are also referred to herein as "compression parameters"), displayed as Q=70 to Q=100 on the top each image. Also listed is the resulting compression ratio, ranging from 37:1 to 6:1. The loss of information resulting from the lower quality factors and resulting higher compression ratios is visually apparent.

The second row of four images displays difference images, where the original image 310 is subtracted from each compressed image so that the error related to compression is displayed for each pixel.

Note that for the Q=70, the difference image demonstrates significant structure as a result of the differences, or "errors", in the compressed image relative to the original image 310. The difference image for the Q=100 image displays very little structure as the difference between the original and Q=100 compressed image is low. The intermediate images demonstrate intermediate degrees of error in the difference images.

Note that these difference images could also be considered "correction" images as they could be subtracted from (or added, if inverted) to the lossy compressed images to correct losses related to compression. In some embodiments, corrections can be applied to some pixels based on compression rules and/or CAP, for example based on anatomic structure, regions, or signal intensity, to cause the lossy compressed image to achieve the desired degree of quality (e.g., to make sure clinically significant information is included in the compressed images).

Figure 3B:
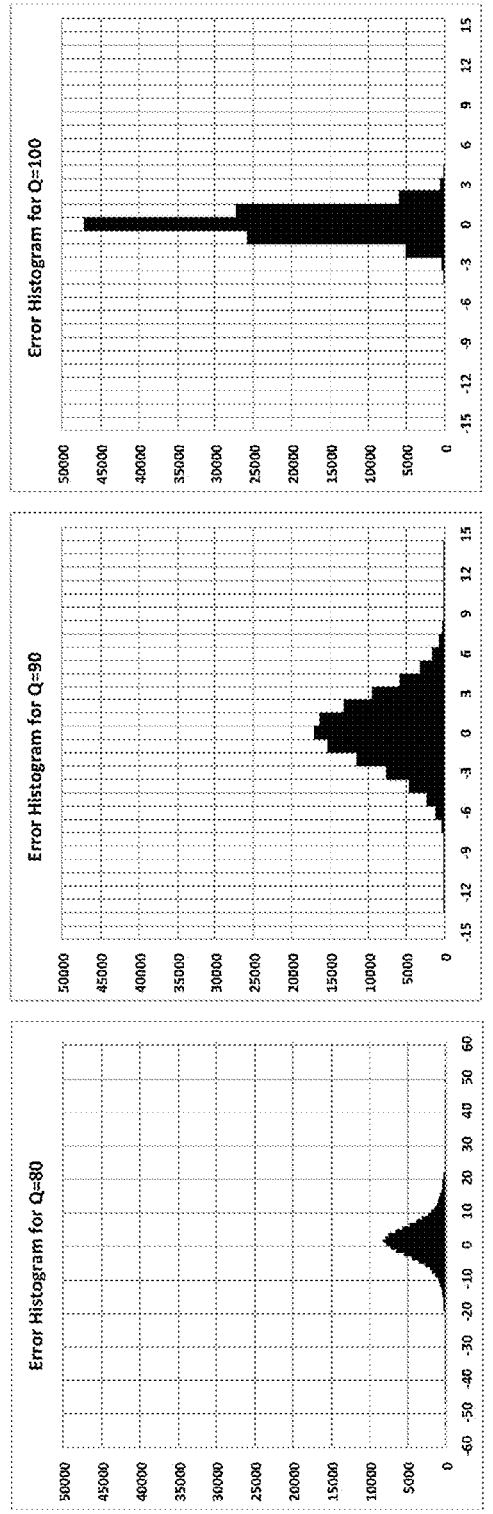

FIGS. 3A-3B are diagrams illustrating various aspects of various example compressed versions of an example digital image 310, according to an embodiment of the present disclosure. FIG. 3A illustrates the original, uncompressed image 310. Superimposed on the image is an oval that defines an area for analysis.

Graph 320 is a histogram which illustrates the results of an analysis of JPEG 2000 lossy compressed images of the original image performed with three different quality factors, Q=80, Q=90 and Q=100 (as illustrated in FIG. 2). The histogram displays a measure of the difference between the original image and the compressed versions, e.g., the error in pixel intensities due to compression. In one embodiment, errors in pixel intensities are calculated for each pixel, as a difference between the pixel intensity in the original uncompressed image 310 and the pixel intensity in a decompressed image generated from the compressed image data. Thus, for an image with 1,048,576 pixels (e.g., a 1024×1024 image), pixel errors may be calculated for each of the 1,048,576 pixels. Graph 320 shows the distribution of these pixels errors. In particular, in graph 320 an error of 0 on the x-axis indicates the number of pixels in the compressed version that are identical in value to the original image. Values to the right and left of 0 display the number of pixels that have for example an error of 1, −1, 2, −2, . . . etc.

Note that for Q=90 compared to Q=100 there are a greater number of pixels that have an error and that the errors are greater. For Q=80, the number of errors and magnitude of the errors are greater. This illustrates one problem with lossy compression, in which the signal intensity of pixels in the lossy compressed image differs from the original image.

FIG. 3B shows further detail of errors for the lossy JPEG 2000 compressed images discussed with reference to FIG. 3A. Diagram 330 is a histogram of compression errors for the image compressed with a quality factor of Q=80, including the mean, minimum, and maximum errors. Diagrams 332 and 334 show results for Q=90 and Q=100 compressed images.

In various implementations, errors may be determined, and/or correction images may be generated, on a pixel-by-pixel basis, and/or based on multiple pixels or groups of pixels at a time, e.g., 4×4 groups of pixels, 6×6 groups of pixels, or the like. Any image processing, compression, generation, segmentation, error determination, and/or analysis (and/or the like) described herein may similarly be performed on a pixel-by-pixel basis, and/or based on multiple pixels or groups of pixels at a time, e.g., 4×4 groups of pixels, 6×6 groups of pixels, or the like.

V. Example Image Segmentation

Figure 4:
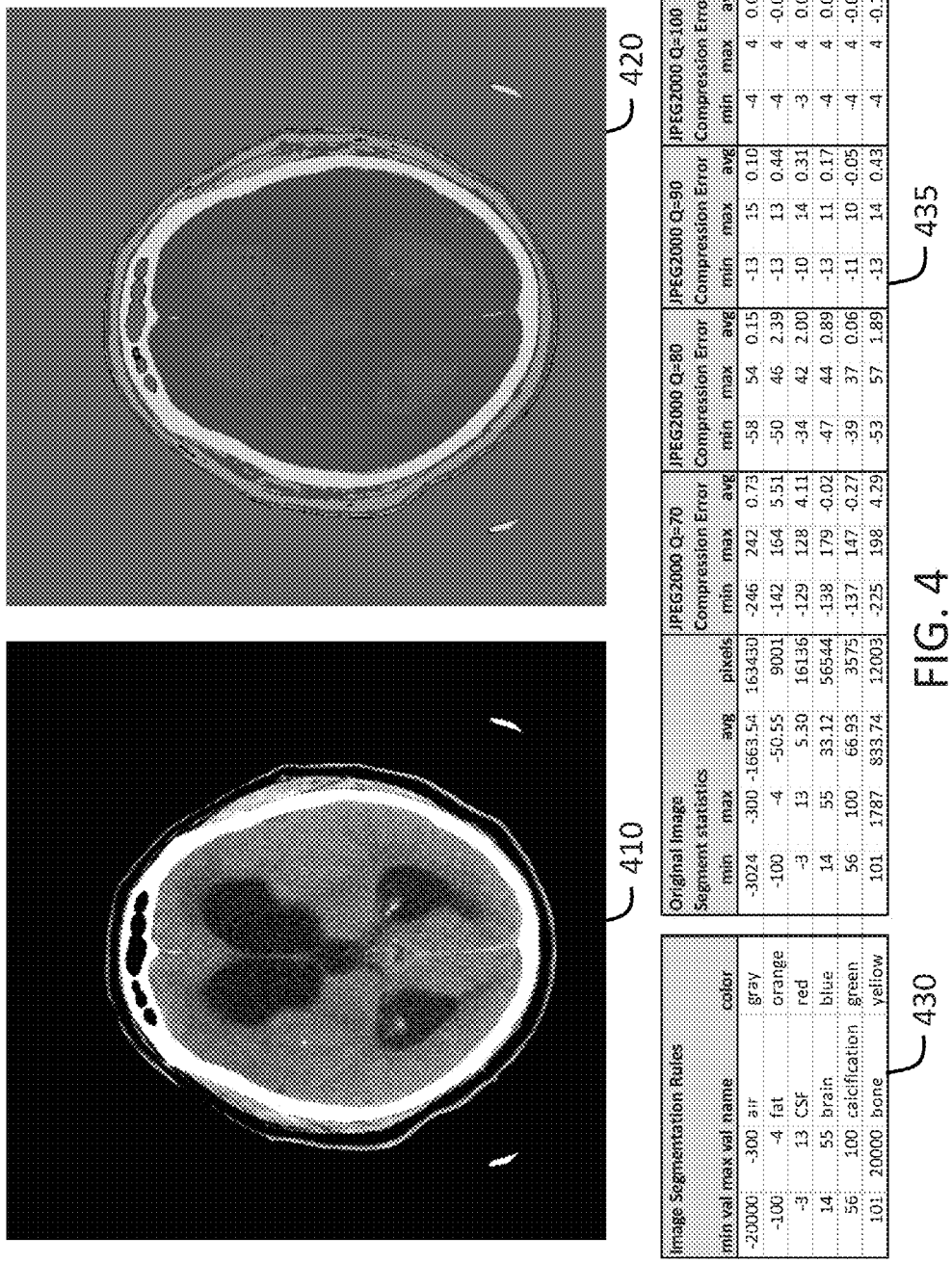
FIG. 4 is a diagram illustrating an example automated segmentation of a digital image, according to an embodiment of the present disclosure.

FIG. 4 is a diagram illustrating an example automated segmentation of a digital image, according to an embodiment of the present disclosure. Automated segmentation may be used to detect various regions within an image so that rules (e.g., compression rules) may treat different regions in an image differently. In some embodiments, rules may apply to specific tissues, structures, or signal intensity ranges, and in those embodiments automated determination of tissues, structure or signal intensity ranges within image may be used to identify such regions. As mentioned above, automated segmentation may be performed by one or more CAP.

In the example of FIG. 4, an example brain CT image is automatically segmented into six different regions that could be used in compression quality rules. Image 410 is an example original, uncompressed image. Image 420 is an image in which different tissues, structures, or signal intensity regions, defined by pixel intensities, have been automatically determined. In the example of image 420, each pixel within the original image was automatically examined and compared with image segmentation rules to determine which tissue type it should be assigned.

Table 430 is an example of image segmentation rules for six tissue types. In the example of Image Segmentation Rules 430, pixels with intensities in the range of −20,000 to −300 are considered to be air and assigned a gray color in the segmented image 420. Pixels in the range of −3 to 13 are assigned to be CSF and displayed in red in the segmented image. Pixels in the range of 101 to 20,000 are assigned to be bone and displayed in yellow. Information for fat, brain, and calcification are also shown in the segmentation rules and the resulting segmented image 420.

In other embodiments, other systems for segmentation could be utilized, for example involving 2D or 3D region growing or anatomic templates.

Table 435 displays information about the regions that have been segmented within image 410.

The original image segment statistics displays the minimum, maximum, and average pixel intensity within the automatically segmented images, as well as the number of pixels within each segmented region. In addition, errors related to compression within the segmented regions are displayed for images compressed with a JPEG 2000 lossy compression algorithm for quality factors (Q) of 70, 80, 90, and 100. For each of those quality factors, statistics are listed for the compression errors, the difference between the original image and the lossy compressed image. Specifically, the range of the error is listed as the minimum and maximum difference between the original and compressed image, as well as the average error. For example, for the Q=80 image, the average error in the CSF region is 2, with individual pixel errors within that region ranging from −34 to 42.

Various methods may be used to segment digital images in the medical imaging context. Examples of such methods are disclosed in the following in journal article: Evan K. Fram, J. David Godwin, and Charles E. Putman, *Three-Dimensional Display of the Heart, Aorta, Lungs, and Airway Using CT*, American Journal of Roentgenology, 139: 1171-1176, December 1982, which is hereby incorporated by reference herein in its entirety. For example, the article describes software that automatically segments tissues to isolate organs (and create 3D displays) of the organs. The segmentation methods discussed in the article, as well as any other currently-known or later developed segmentation techniques may be used in conjunction with the systems and methods discussed herein.

VI. Example Compression Rules

Figure 5A:
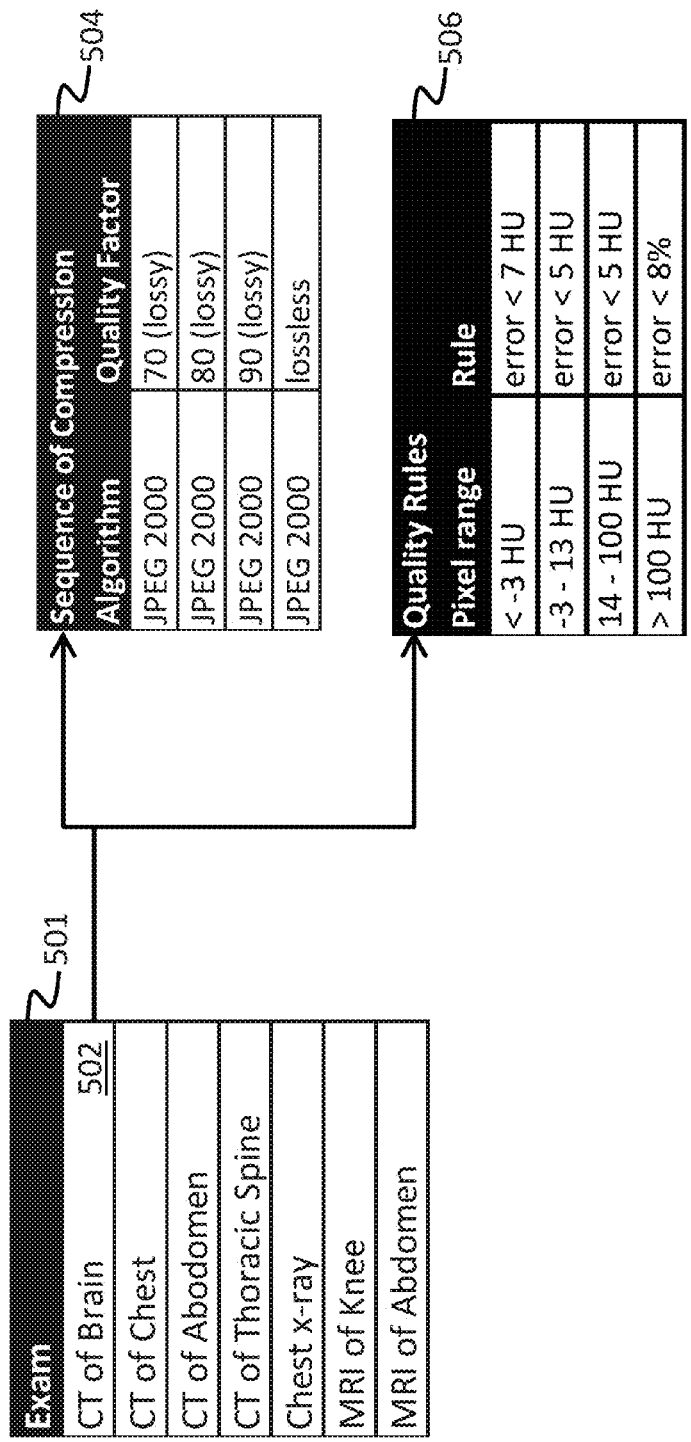
FIGS. 5A-5C are diagrams illustrating example compression rules, according to various embodiments of the present disclosure.
Figure 5B:
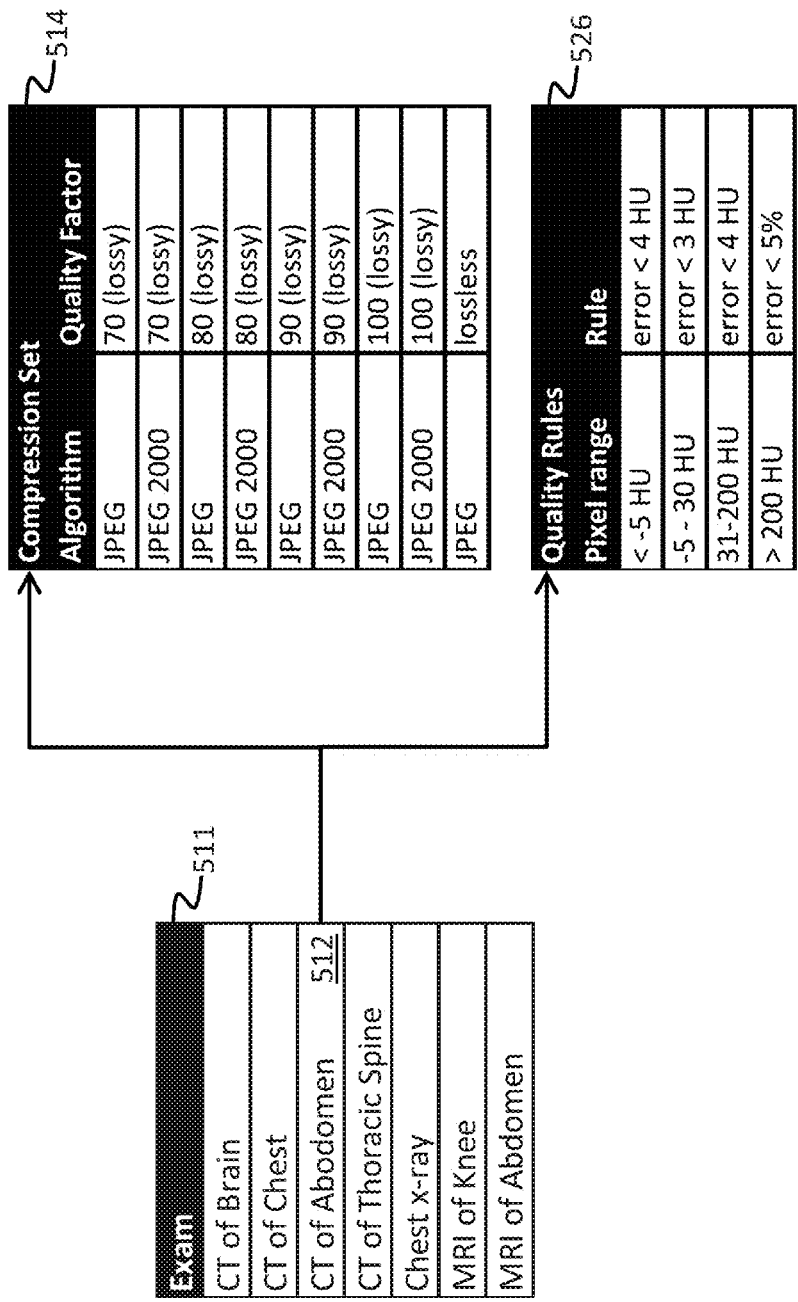
Figure 5C:
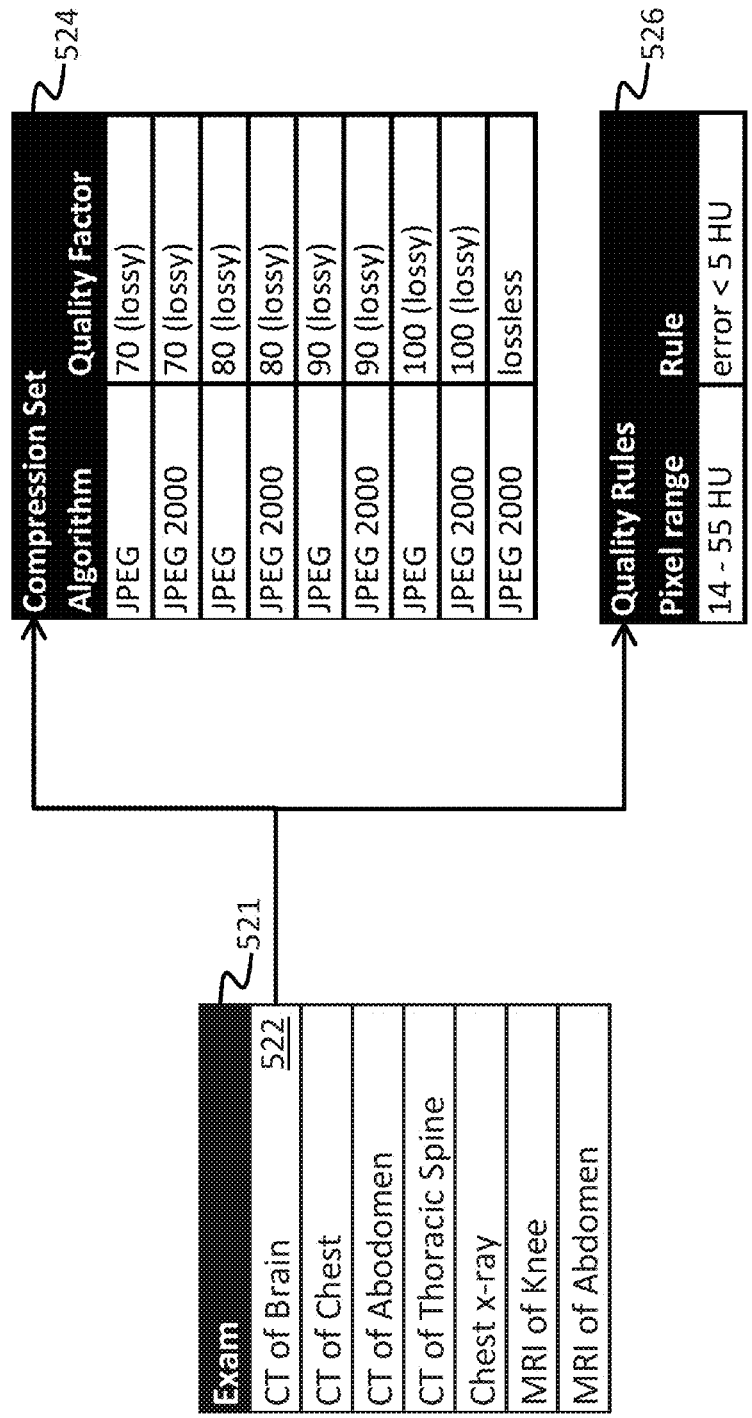

FIGS. 5A-5C are diagrams illustrating example compression rules, according to various embodiments of the present disclosure. As described above, compression rules may be associated with one or more image characteristics.

In reference to FIG. 5A, compression rules are shown that are associated with exam types (e.g., modality, acquisition type, and/or anatomical feature). For example, table 501 shows a list of exam types. In one embodiment the list may include other image characteristics, such as clinical information, so that rules may, for example, be specific for various clinical indications (e.g. CT of Brain to evaluate brain tumor), users, groups, imaging parameters, particular imaging devices, etc.

In the example shown, entry 502, "CT of Brain," is associated with example rules consisting of Sequence of Compression table 504 listing compression parameters in the order they are to be tested, as well as example Quality Rules table 506, listing quality requirements for the compressed image.

The application of these rules is discussed with reference to the embodiment of FIG. 6.

FIG. 5B is another example of compression rules, similar to the example of FIG. 5A, but associated with entry 512 for CT of Abdomen. In addition, the rules include a Compression Set table 514, rather than a Sequence of Compression table as in the example of FIG. 5A. In this example, multiple compression algorithms are used in order to identify the optimal compression for images. In other embodiments, even additional compression techniques and/or parameters for those compression techniques may be included in rules for one or more exam types and/or other image characteristics.

The example rules illustrated in FIG. 5B will be discussed with reference to the embodiment of FIG. 7.

FIG. 5C is another example of compression rules. The example rules illustrated in FIG. 5C will be discussed with reference to the embodiment of FIG. 8.

VII. Example Methods

Figure 7:
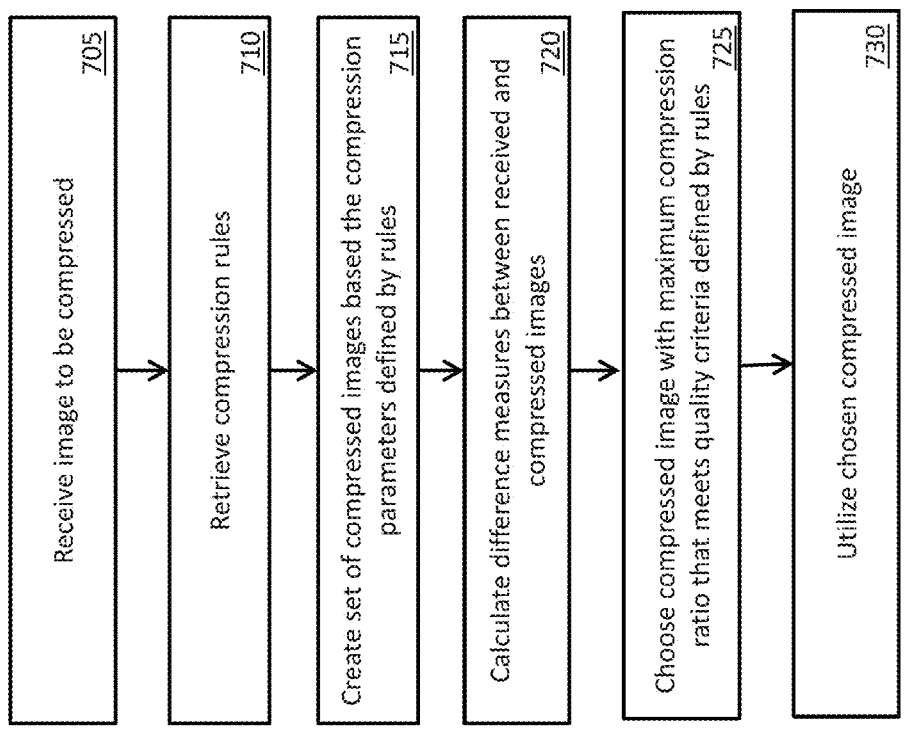
Figure 8:
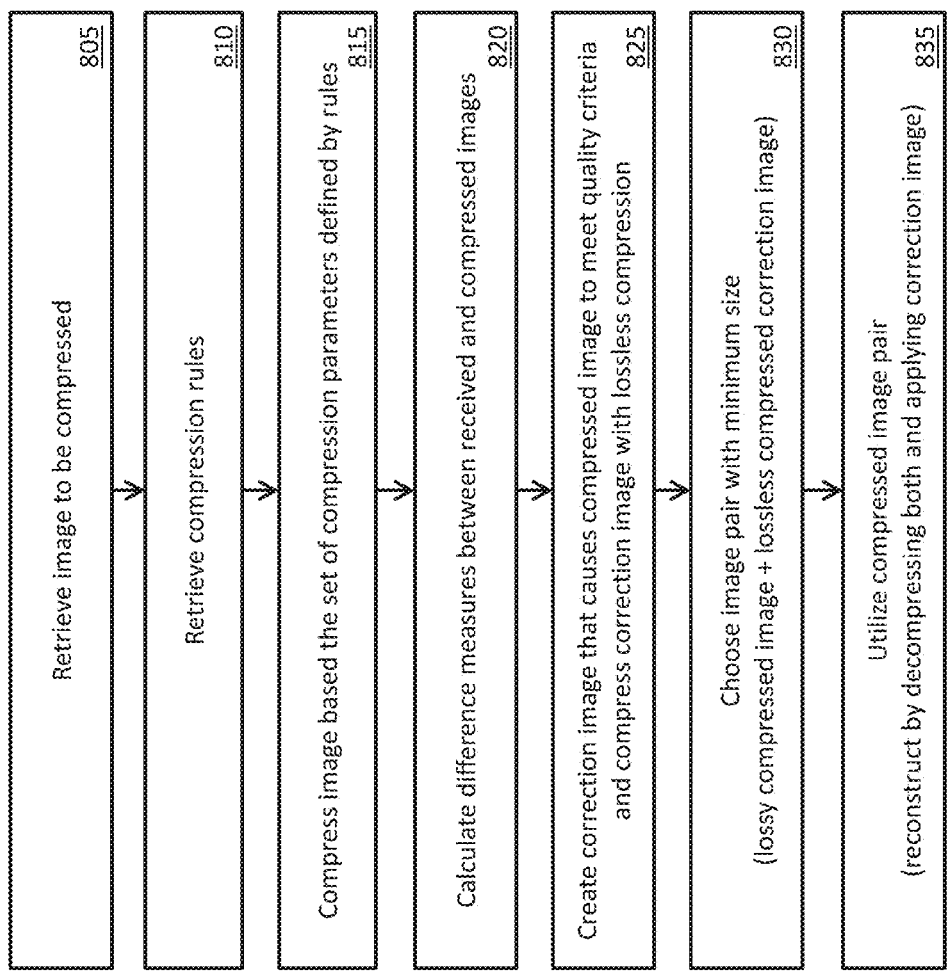

FIGS. 6-8 are flowcharts illustrating example methods of compressing digital images, according to various embodiments of the present disclosure. The methods of FIGS. 6-8, as well as other processes discussed herein, may be performed, e.g., by the computing system 150, such as by accessing images stored on the image server 120, and executing compression rules stored in the compression rules database 124 by the rules engine 163. In some embodiments, the rules engine 163 and/or compression rules database 124 are part of the compression computing device (e.g. stored on the memory/storage 153 of the compression computing device and/or are available via a local area network coupled to the compression computing device 115). In other embodiments, any of these methods may be performed by other computing devices or systems. Depending on the embodiment, the methods illustrated in flowcharts may include fewer or additional blocks and/or the blocks may be performed in an order different than is illustrated.

a. Example Method Including Generation of a Compressed Image

The flowchart of FIG. 6 illustrates an embodiment that may be used in conjunction with compression rules. The blocks are discussed with reference to the example compression rules illustrated in FIG. 5A, but other compression rules may be utilized.

At block 601, an image to be compressed is received, retrieved, and/or accessed, such as from the image server 120, PACS 121, or any other source. In one embodiment, image characteristics associated with the image and/or an exam associated with the image and/or the user/group/site may also be retrieved and/or otherwise determined. These image characteristics may include, for example, Modality, e.g., CT, MRI, PET, etc.

Technical parameters associated with the image, such as slice thickness, image resolution, MRI sequence parameters, etc.

Clinical information, such as clinical indication, age, gender, etc.

User, group, or site compression rule preferences.

And/or any other image characteristics as described above.

At block 605, compression rules relevant to the image and/or information associated with the image (e.g., image characteristics) or exam and/or user/group/site are retrieved. For example, if the image were an image or images associated with a CT of the Brain, example rules illustrated in FIG. 5A could be retrieved, including "Sequence of Compression" table 504 and Quality Rules 506

At block 610, the initial compression parameters are retrieved. In the example of table 504, the initial compression parameters are to use JPEG 2000 lossy compression with a Quality Factor of 70.

At block 615, the image is compressed with the current compression parameters, in this example using JPEG 2000 lossy compression with a Quality Factor of 70, as discussed in the prior block.

At block 620, the compressed image is compared to the original (e.g., uncompressed) image and the difference is calculated to determine errors related to compression. For example, differences between the original image and the compressed image may be calculated as described above in reference to FIGS. 2, 3A-3B, and 4.

At block 625, the errors calculated in at block 620 are compared to the retrieved Quality Rules to determine whether or not the compressed image is acceptable (e.g., significant information of the compressed image is not lost as a result of the compression). In the example of the Quality Rules illustrated in table 506, in order for the compressed image to be acceptable all of the quality criteria listed must be met. For example, the second rule indicates that pixels with values between −3 and 13 in the original image must have an error of <5 HU, e.g., the value of each pixel in the compressed image must differ by less than 5 from the corresponding pixels in the original image for pixels in the original image that have values of −3 to 13. These quality rules also indicate acceptable errors in pixels having other value ranges within the original image.

If the quality of the compressed image is acceptable (e.g., all of the quality rules in table 506 are met by the compressed image), then at block 635, the compressed image is utilized, for example by storing it or transmitting it.

If the quality is not acceptable, then at block 630, the next compression parameters to try are chosen. In the example of 'Sequence of Compression" table 504, the next compression parameters to try would be JPEG 2000 lossy compression with a Quality Factor of 80. Note that if the Quality Factors of 70, 80, and 90 are tried and the quality is not acceptable, the final parameter in the table is utilized, "JPEG lossless" which guarantees that there are no errors in the compressed image.

After the next compression parameters are chosen, the sequence returns to block 615.

If compression is acceptable, than at block 635, the compressed image is utilized, for example for transmission or storage.

In one embodiment, different compression parameters may be used for each image in a series and/or an exam. In another embodiment, the same compression parameters are used for every image in a series or exam. In those cases, the highest quality compression, e.g., highest quality factor, that is required for every image in a series or exam is utilized for all images in a series or exam. This technique of using the same compression parameters for all images in a series or exam can be applied to other embodiments, such as those discussed with reference to FIGS. 7 and 8.

Advantageously, according to the example of FIG. 6, the system may efficiently generate a compressed image that satisfies quality rules (e.g., in which significant information is not lost). Compressed images are generated and tested in series such that, once a compressed image satisfies the quality criteria, the system need not continue and the compressed image can be stored or sent. This process may save processor power as many compressed images do not need to be generated. Further, generation of the compressed image is tied to the functioning of the processor of the computing system 150, as the compressed image is generated by analysis of each pixel of the image, and compression of the pixels of the image.

b. Example Method Including Generation of Multiple Compressed Images

FIG. 7 is another embodiment of a method for compressing images based on quality rules. The blocks illustrated are discussed with reference to the example rules illustrated in FIG. 5B.

At block 705, an image or images are received, retrieved, and/or accessed, such as from the image server 120, PACS 121, or any other source.

At block 710, compression rules are retrieved that apply to the image or images received (as described above).

At block 715, a set of compressed images is created based on the compression rules. As shown in the example rules illustrate in FIG. 5B, Compression Set table 514 lists a set of nine compression techniques, ranging from JPEG lossy with a quality factor of 70 to JPEG lossless compression, including compression by both JPEG and JPEG 2000 compression algorithms. In the embodiment of FIG. 7, each of the listed compression techniques and quality factors (and/or compression ratios or other compression parameters in other embodiments) are performed on the image (or images), rather than performing one compression technique at a time until a suitable compression technique is identified, such as might be performed with the method of FIG. 6.

At block 720, each of the compressed images, in this example nine, are compared to the original image to identify differences between the original images and compressed images, such as by determining pixel errors between the compressed images and the original image (as described above).

At block 725, the errors within the compressed images are compared to the Quality Rules 526 and the compressed image that meets these quality rules (e.g., significant information of the compressed image is not lost as a result of the compression) and has the highest compression ratio (smallest size) is automatically selected.

At block 730, the image chosen in the prior block is utilized, for example for transmission or storage.

Advantageously, according to the example of FIG. 7, the system may efficiently generate a compressed image that satisfies quality rules (e.g., in which significant information is not lost). Multiple compressed images are generated and tested in parallel such that a maximum compressed image (that satisfies the quality criteria) may be quickly determined, and the compressed image can be stored or sent. This process may save processor time as multiple compressed images do not need to be generated in series, but may be generated in parallel. Further, generation of the compressed image is tied to the functioning of the processor of the computing system 150, as the compressed image is generated by analysis of each pixel of the image, and compression of the pixels of the image.

c. Example Method Including Generation of a Correction Image

FIG. 8 is another embodiment of a method for compressing images but maintaining quality as defined by rules. The blocks illustrated are discussed with reference to the example rules illustrated in FIG. 5C.

At block 805, an image or images are received, retrieved, and/or accessed, such as from the image server 120, PACS 121, or any other source.

At block 810, compression rules are retrieved that apply to the image or images received (as described above).

At block 815, a set of compressed images is created based on the compression rules. As shown in the example rules illustrated in FIG. 5C, Compression Set table 524 lists a set of nine compression techniques, ranging from JPEG lossy with a quality factor to 70 to JPEG 2000 lossless compression.

At block 820, each of the compressed images, in this example nine, are compared to the original image and the differences between the original images and compressed images are determined (as described above).

At block 825, the errors within the compressed images are compared to the Quality Rules 526 and a set of Correction Images are generated. The respective Correction Images are generated such that, when added to the respective compressed images, the Correction Images correct the errors in the compressed images on a pixel by pixel basis (or based on multiple pixels or groups of pixels at a time, e.g., 4×4 groups of pixels, 6×6 groups of pixels, or the like). Thus, for example, adding a Correction Image to its associated compressed image results in the original image and, thus, would meet the Quality Rules.

In some embodiments, correction using the correction image may be applied to only certain portions, structures, regions, or signal intensity regions of an image. In the example of Quality Rules 526, the correction image only applies to pixels that have signal intensities in the original image in the range of 14-55 HU, approximately correlating with brain tissue, as illustrated in blue in the automatic segmentation image 420 of FIG. 4.

Figure 9:
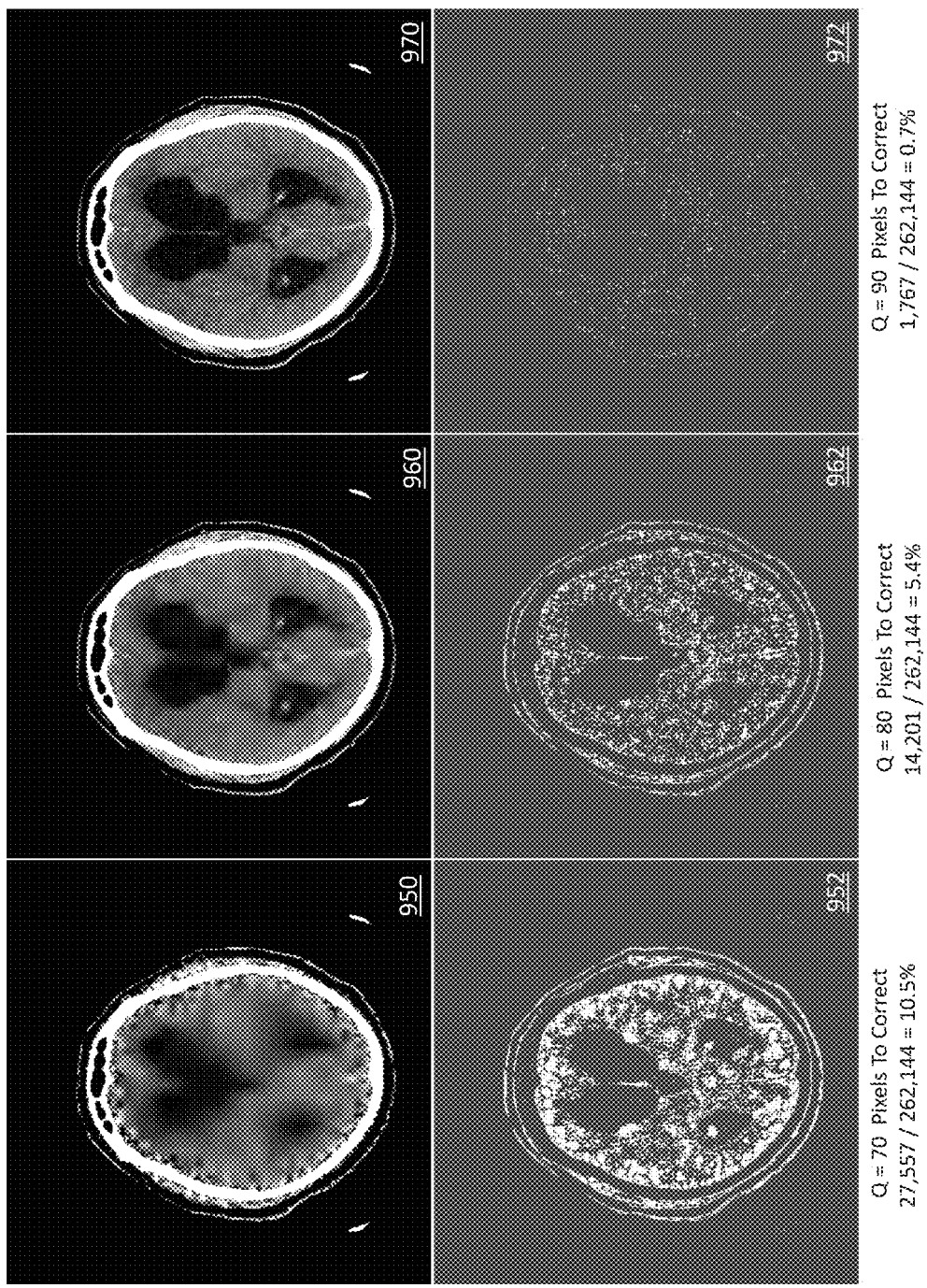
FIG. 9 is a diagram illustrating various example compressed versions of an example digital image, according to an embodiment of the present disclosure.

As described below with reference to FIG. 9, images 952, 962, and 972 of FIG. 9 illustrate the specific pixels that would contain information in the example correction images. The majority of pixels in each correction image would be 0 so the correction images would be highly compressible with lossless techniques. The correction image may be compressed using a lossless compression technique, for example ZIP, RLE, JPEG 2000 lossless, or JPEG lossless. In one embodiment, the correction image is compressed with a number of different lossless techniques and the one chosen is the one that results in the smallest size.

At block 830, the pair of lossy compressed original image and lossless compressed correction image with the smallest size is automatically selected.

At block 835, the image pair chosen in block 830 is utilized, for example for transmission or storage.

When the compressed image is to be used later, for example for viewing by a user, the image may be reconstructed by decompressing the image and correction image and then applying the correction image to the original compressed image, for example by adding the two images on a pixel by pixel bases.

In another embodiment, the original image may be modified before compression (preprocessed) so that once compressed using lossy compression, the compressed image would pass the quality rules. In one embodiment, this could be an iterative process.

In an embodiment, portions of an image requiring a lower pixel error rate, such as brain tissue, may be corrected by applying the brain tissue segmented portions of the correction image to the compressed image prior to display or transmission to a viewing device. In this embodiment, only this selectively corrected image may be transmitted, stored, and/or displayed, rather than the pair of compressed image and error image.

Advantageously, according to the example of FIG. 8, the system may efficiently generate a compressed image (and/or a compressed image and a correction image) that satisfies quality rules (e.g., in which significant information is not lost). Multiple compressed images, and their respective correction images, are generated and tested in parallel such that a maximum compressed image (that satisfies the quality criteria) may be quickly determined, and the compressed image (and, optionally, the correction image) can be stored or sent. This process may save processor time as multiple compressed images and correction images do not need to be generated in series, but may be generated in parallel. Further, generation of the compressed image is tied to the functioning of the processor of the computing system 150, as the compressed image is generated by analysis of each pixel of the image, and compression of the pixels of the image.

d. Example Correction Images

FIG. 9 is a diagram illustrating various example compressed versions of an example digital image, according to an embodiment of the present disclosure. FIG. 9 illustrates example compressed images 950, 960, and 970, which are JPEG 2000 lossy compressed images with quality factors of 70, 80, and 90, respectively.

Below to those images are respective correction images 952, 962, and 972, where each pixel that would have a non-zero value is displayed as white and those with zero values are displayed in blue. Thus the example images illustrate pixels in white that are to be corrected based on the quality rules; in this example, the example quality rules illustrated in FIG. 5C (e.g., range of 14-55 with error $>=5$ HU).

Below each correction image is displayed the number of pixels that are corrected in the correction image and the percentage of images in each lossy compressed image that require correction based on the quality rules of FIG. 5C. For example, for the JPEG 2000 lossy compressed image compressed with a Quality Factor=90 (image 970), only 0.7% of the pixels in the correction image 972 are non-zero, so that the correction image will be highly compressible with a lossless compression technique, adding relatively little in size to the pair of the lossy compressed image and correction image.

VIII. Example Computing Systems

Referring again to FIG. 1, various configurations of the computing system 150 and network environment 100 may be used to implement and/or accomplish the systems and methods disclosed herein. For example, the computing system 150 may be configured to display and/or enable a user to view and/or interact with various types of data including digital images and/or other types of information, as described above.

As described above, the computing system may take various forms. In one embodiment, the computing system 150 may be an information display computing device and/or system, a server, a computer workstation, a desktop computer, a Picture Archiving and Communication System (PACS) workstation, a laptop computer, a mobile computer, a smartphone, a tablet computer, a wearable computer (for example, a head-mounted computer and/or a computer in communication with a head-mounted display), a smartwatch, a mobile computer, a cell phone, a personal digital assistant, a gaming system, a kiosk, an audio player, and/or any other device that utilizes a graphical user interface, such as office equipment, automobiles, airplane cockpits, household appliances, automated teller machines, self-service checkouts at stores, information and other kiosks, ticketing kiosks, vending machines, industrial equipment, and/or a television, for example. In an embodiment the computing system 150 comprises one or more computing devices in communication with one another.

The computing system 150 may include various components including, for example, one or more processors 152, memory and/or data storage 153 (including one or more software modules 151 and/or a rules engine 163 (which may itself comprise a software module)), an operating system 154, a display 155, one or more input devices 156, and/or one or more interfaces 157. Each of the components of the computing system 150 may be connected and/or in communication with each other using, for example, a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing system 150 (as described above and below) may be combined into fewer components and modules or further separated into additional components and modules.

In various embodiments the software modules 151 may provide functionality as described above with reference to the various figures. For example, modules 151 of the computing system 150 may include user input modules, image display modules, compression modules, rules engine modules (for example, rules engine 163), user interface modules, and/or the like. For example, the compression and/or rules engine modules may implement the functionality and techniques described above. Further, the image display modules and/or the user interface modules may display user interfaces, images, and/or other data on the display 155 in response to user inputs (as described in reference to various embodiments of the present disclosure). Further, the image display modules and/or the user interface modules may be configured and/or designed to generate user interface data useable for rendering the interactive user interfaces described herein, such as a web application and/or a dynamic web page displayed by a computing device. In various embodiments the user interface data may be used by the computing system 150, and/or communicated to any other computing device, such that the example user interfaces are displayed to a user. For example, the user interface data may be executed by a browser (and/or other software program) accessing a web service and configured to render the user interfaces based on the user interface data.

The rules engine 163 may operate in conjunction with the other modules to perform various functionality of the data navigation systems described above. For example, the rules engine 163 may determine, based on one or more rules of the compressions rules database 124, to compress an image using a certain compression technique and/or using certain compression parameters, as described above. As also described above, rules that may be executed by the rules engine 163 may include various other types of rules, including segmentation rules.

As described below, the software modules 151 may include various software instructions, code, logic instructions, and/or the like that may be executed by the one or more processors 152 to accomplish the functionality described above. In other embodiments, software modules 151 may reside on another computing device and/or system, such as a web server or other server (for example, server 120) or other server, and a user may directly interact with a second computing device and/or system that is connected to the other computing device and/or system via a computer network.

The computing system 150 may run an off-the-shelf operating system 154 such as a Windows, Linux, MacOS, Android, or iOS, or mobile versions of such operating systems. The computing system 150 may also run a more specialized operating system which may be designed for the specific tasks performed by the computing system 150, or any other available operating system.

The computing system 150 may include one or more computer processors 152, for example, hardware computer processors. The computer processors 152 may include central processing units (CPUs), and may further include dedicated processors such as graphics processor chips, or other specialized processors. The processors may be used to execute computer instructions based on the software modules 151 to cause the computing system 150 to perform operations as specified by the modules 151. The software modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, Objective-C, Swift, JavaScript, ActionScript, Visual Basic, HTML, Lua, C, C++, or C#. While "modules" are generally discussed herein with reference to software, any modules may alternatively be represented in hardware or firmware. In various embodiments, the modules described herein refer to logical modules that may be combined with other modules or divided into sub-modules despite their physical organization or storage.

The computing system 150 may also include memory 153. The memory 153 may include volatile data storage such as RAM or SDRAM. The memory may also include more permanent forms of storage such as a hard disk drive, a flash disk, flash memory, a solid state drive, or some other type of non-volatile storage, as described below.

The computing system 150 may also include or be interfaced to one or more display devices that provide information to the users. Display devices 155 may include a video display, such as one or more high-resolution computer monitors, or a display device integrated into or attached to a laptop computer, handheld computer, smartphone, smartwatch, wearable computer, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers. As described above, images and other information may be displayed to the user via the display devices 155 such that the user may efficiently view and interact with such images and information.

The computing system 150 may also include or be interfaced to one or more input devices 156 which receive input from users, such as a keyboard, trackball, mouse, 3D mouse, dial and/or knob (for example, a smartwatch crown), drawing tablet, joystick, game controller, touch sensitive surface (for example, capacitive or resistive touch screen), touchpad, accelerometer, video camera and/or microphone.

The computing system 150 may also include one or more interfaces 157 which allow information exchange between the computing system 150 and other computers and input/output devices using systems such as Ethernet, Wi-Fi, Bluetooth, as well as other wired and wireless data communications techniques.

In various embodiments, the functionality provided by the imaging device/scanner 110, the PACS 121, the PACS workstation 122, the image server 120, and/or the compression rules database 124, may reside within computing system 150.

The computing system 150 may communicate and/or interface with other systems and/or devices. In one or more embodiments, the computing system 150 may be connected to the computer network 190. The computer network 190 may take various forms. For example, the computer network 190 may be a wired network or a wireless network, or it may be some combination of both. The computer network 190 may be a single computer network, or it may be a combination or collection of different networks and network protocols. Additionally, the computer network 190 may include one or more local area networks (LAN), wide area networks (WAN), personal area networks (PAN), cellular or data networks, and/or the Internet.

Various devices and subsystems may be connected to the network 190. As shown in FIG. 1, for example, the computing system 150 may be in communication with the imaging device/scanner 110, the PACS 121, the PACS workstation 122, the image server 120, and/or the compression rules database 124. Image server 120 include a database, data store, and/or other electronic or computer-readable medium storage device configured to store, for example, digital images and/or other data. Such images and/or other data may be processed, for example, by the server 120 and/or the computing system 150. Further, the various components of the network environment 100 may be in communication with various other devices that may, for example, capture and provide images and/or other data to the computing system 150. For example, imaging device/scanner 110 may include one or more medical scanners may be connected, such as MRI scanners. The MRI scanner may be used to acquire MRI images from patients, and may share the acquired images with other devices on the network 190. The imaging device/scanner 110 may also include one or more CT scanners and/or X-Ray scanners. The CT scanners and/or X-Ray scanners may also be used to acquire images and, like the MRI scanner, may then store those images and/or share those images with other devices via the network 190. Any other scanner or device capable of inputting or generating information that may be presented to the user as images, graphics, text, sound, video, etc. may be connected to the network 190, including, for example, computing systems used in the fields of ultrasound, angiography, nuclear medicine, radiography, endoscopy, pathology, dermatology, and the like.

Also connected to the network 190 may be a Picture Archiving and Communications System (PACS) 121 and/or PACS workstation 122. The PACS System 121 may be used for the storage, retrieval, distribution and presentation of images (such as those created and/or generated by the MRI scanner and/or CT Scanner). The medical images may be stored in an independent format, an open source format, or some other proprietary format. A common format for image storage in the PACS system is the Digital Imaging and Communications in Medicine (DICOM) format. In various embodiments, the stored images may be transmitted digitally via the PACS system, often reducing or eliminating the need for manually creating, filing, or transporting film jackets.

The network 190 may also be connected to a Radiology Information System (RIS). In an embodiment, the radiology information system may be a computerized system that is used by radiology departments to store, manipulate and distribute patient radiological information.

Also attached to the network 190 may be an Electronic Medical Record (EMR) system. The EMR system may be configured to store and make accessible to a plurality of medical practitioners computerized medical records. Also attached to the network 190 may be a Laboratory Information System. In an embodiment, the Laboratory Information System may be a software system which stores information created or generated by clinical laboratories. Also attached to the network 190 may be a Digital Pathology System that may be used to digitally manage and store information related to medical pathology.

Also attached to the network 190 may be one or more Computer Aided Diagnosis Systems (CAD) systems that are generally used to perform Computer-Aided Processing (CAP) such as, for example, CAD processes. In one embodiment, the CAD systems functionality may reside in a computing device and/or system separate from computing system 150 while in another embodiment the CAD systems functionality may reside within computing system 150.

Also attached to the network 190 may be one or more Processing Systems that may be used to perform computerized advanced processing such as, for example, computations on imaging information to create new views of the information, for example, volume rendering and/or other types of processing, for example image enhancement, volume quantification, blood-flow quantification, and the like. In one embodiment, such processing functionality may reside in a computing device and/or system separate from computing system 150 while in another embodiment the processing functionality may reside within computing system 150.

In other embodiments, other computing devices and/or systems that store, provide, acquire, and/or otherwise manipulate medical data may also be coupled to the network 190 and may be in communication with one or more of the devices illustrated in FIG. 1, such as with the computing system 150.

Depending on the embodiment, other devices discussed herein may include some or all of the same components discussed above with reference to the computing system 150 and may perform some or all of the functionality discussed herein.

As mentioned above, various of the components of the network environment 100 of FIG. 1 described above may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

IX. Additional Embodiments

Any of the processes, methods, algorithms, elements, blocks, applications, or other functionality (or portions of functionality) described in the preceding sections may be embodied in, and/or fully or partially automated via, modules, segments, and/or portions of software code and/or logic instructions which include one or more executable instructions (as described below) executed by one or more computer systems or computer processors comprising computer hardware. Further, and/or alternatively, any of the processes, methods, algorithms, elements, blocks, applications, or other functionality (or portions of functionality) described in the preceding sections may be embodied in, and/or fully or partially automated via, electronic hardware such as application-specific processors (e.g., application-specific integrated circuits (ASICs)), programmable processors (e.g., field programmable gate arrays (FPGAs)), application-specific circuitry, logic circuits, and/or the like (any of which may also combine custom hard-wired logic, ASICs, FPGAs, etc. with custom programming/execution of software instructions to accomplish the techniques). For example, the various illustrative logical blocks, methods, routines, and the like described in connection with the embodiments disclosed herein may be implemented as electronic hardware, computer software, or combinations of both. To illustrate this, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

For example, the functionality described herein may be performed as software instructions are executed by, and/or in response to software instruction being executed by, one or more hardware processors and/or any other suitable computing devices. The software instructions and/or other executable code may be read from a non-transitory or tangible computer-readable medium.

The terms "non-transitory medium," "non-transitory computer-readable medium," "tangible computer-readable storage medium," and similar terms, as used herein are synonymous with the term "data store," and are broad terms encompassing their ordinary and customary meanings, and include any data stores and/or mediums that store data and/or instructions that cause a machine (e.g., a computing device) to operate in a specific fashion. Such non-transitory mediums may comprise non-volatile mediums and/or volatile mediums. Non-volatile mediums include, for example, optical or magnetic disks. Volatile mediums include, for example, dynamic memory (e.g., random-access memory (RAM)). Common forms of non-transitory mediums include, for example, floppy disks, flexible disks, hard disks, solid state drives, magnetic tape, or any other magnetic data storage medium, a CD-ROM, a DVD-ROM, any other optical data storage medium, any physical medium with patterns of holes, a RAM, a PROM, an EPROM, a FLASH-EPROM, NVRAM, any other memory chip or cartridge, and networked versions of the same. Non-transitory mediums are distinct from, but may be used in conjunction with, transmission mediums. Transmission mediums participate in transferring information between non-transitory mediums. For example, transmission mediums include coaxial cables, copper wire, and fiber optics, including wires that comprise busses and/or the like within certain computing devices. Transmission mediums may also take the form of acoustic or light waves, such as those generated during radio-wave and infra-red data communications.

Accordingly, a software instruction and/or module may reside in RAM memory, flash memory, ROM memory, hard disk, solid state drive, CD-ROM, DVD-ROM, and/or any other form of a non-transitory computer-readable storage medium. Various forms of mediums may be involved in carrying one or more sequences of one or more instructions to computer processors (of the present disclosure) for execution. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

Any of the above-mentioned processors, and/or devices incorporating any of the above-mentioned processors, may be referred to herein as, for example, "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program. In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

In general, the terms "code," "instructions," "module," "application," "software application," and/or the like, as used herein, refer to a collection of software instructions, possibly having entry and exit points, written in a programming language, such as, for example, Java, Lua, C or C++. Such software may be compiled and linked into an executable program, installed in a dynamic link library, or may be written in an interpreted programming language such as, for example, BASIC, Perl, or Python. It will be appreciated that such software instructions may be callable from other software instructions or from itself, and/or may be invoked in response to detected events or interrupts. Software instructions configured for execution on computing devices may be provided on a computer readable medium (e.g., a non-transitory computer readable medium), and/or as a digital download (and may be originally stored in a compressed or installable format that requires installation, decompression or decryption prior to execution) that may then be stored on a computer readable medium (e.g., a non-transitory computer readable medium). Such software instructions may be stored, partially or fully, on a memory device (e.g., a non-transitory computer readable medium) of the executing computing device, for execution by the computing device.

Alternate implementations are included within the scope of the embodiments described herein in which certain elements or functions may be deleted, executed out of order from that shown or discussed, including substantially concurrently (for example, through multi-threaded processing, interrupt processing, or multiple processors or processor cores or on other parallel architectures) or in reverse order, depending on the functionality involved. Further, the various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A system comprising:
a non-transitory computer readable storage medium having software instructions embodied thereon; and
one or more processors configured to execute the software instructions to cause the one or more processors to:
compress a digital image using each of a plurality of compression algorithms, in parallel, to generate a set of compressed digital images that are compressed at a plurality of different compression levels;
for each of the compressed digital images of the set, determine a respective amount of errors based on comparison of the respective compressed digital images to the digital image; and
determine a first compressed digital image of the set that is compressed at a highest compression level of the plurality of compression levels that also has an amount of errors that satisfies a threshold.

2. The system of claim 1, wherein the one or more processors are configured to execute the software instructions to cause the one or more processors to further:
determine characteristic associated with the digital image;
determine a compression rule associated with the characteristic; and
determine the threshold based on the compression rule,
wherein the characteristic associated with the digital image includes at least one of: an imaging modality, an anatomical feature, or an acquisition type.

3. The system of claim 1, wherein the plurality of compression algorithms includes a plurality of quality factors, and the set of compressed digital images is generated based on the respective compression algorithms and quality factors.

4. The system of claim 1, wherein determining an amount of errors by comparison of a compressed digital image to the digital image comprises:
determining a difference between the digital image and the compressed digital image to generate difference image data; and
determining the amount of errors by at least one of:
determining a number of pixels in the difference image data having a value indicative of an error, or
determining a degree of error in one or more pixels of the difference image data.

5. The system of claim 1, wherein determining an amount of errors by comparison of a compressed digital image to the digital image comprises:

identifying one or more pixels of the digital image having an intensity value satisfying a second threshold;

for each pixel of the one or more pixels, determining a difference between the pixel of the digital image and the pixel of the compressed digital image to generate difference image data;

determining the amount of errors by at least one of:
  determining a number of pixels in the difference image data having a value indicative of an error, or
  determining a degree of error in one or more pixels of the difference image data.

6. The system of claim 5, wherein each of the one or more pixels comprises a group of pixels, and wherein each group of pixels comprises at least one of: a 4×4 group of pixels, or a 6×6 group of pixels.

7. The system of claim 1, wherein determining an amount of errors by comparison of a compressed digital image to the digital image comprises:
  identifying one or more regions of the digital image having pixel intensity values satisfying a second threshold;
  for each pixel or group of pixels of the one or more regions, determining a difference between the pixel of the digital image and the pixel of the compressed digital image to generate difference image data; and
  determining the amount of errors by at least one of:
    determining a number of pixels in the difference image data having a value indicative of an error, or
    determining a degree of error in one or more pixels of the difference image data.

8. The system of claim 1, wherein the one or more processors are configured to execute the software instructions to cause the one or more processors to further:
  in response to determining that none of the compressed digital images of the set is associated with an amount of errors that satisfies the threshold, recompress the digital image using a lossless compression technique to generate a second compressed digital image; and
  store the second compressed digital image in a data store.

9. The system of claim 1, wherein the highest compression level is a compression level that requires a least amount of storage space as compared to other compression levels of the plurality of compression levels, while also having the amount of errors that satisfies the threshold.

10. A computer-implemented method comprising:
  by one or more processors executing program instructions:
    compressing a digital image using each of a plurality of compression algorithms, in parallel, to generate a set of compressed digital images that are compressed at a plurality of different compression levels;
    for each of the compressed digital images of the set, determining a respective amount of errors based on comparison of the respective compressed digital images to the digital image; and
    determining a first compressed digital image of the set that is compressed at a highest compression level of the plurality of compression levels that also has an amount of errors that satisfies a threshold.

11. The computer-implemented method of claim 10, further comprising:
  by the one or more processors executing program instructions:
    determining characteristic associated with the digital image;
    determining a compression rule associated with the characteristic; and
    determining the threshold based on the compression rule,
    wherein the characteristic associated with the digital image includes at least one of: an imaging modality, an anatomical feature, or an acquisition type.

12. The computer-implemented method of claim 10, wherein the plurality of compression algorithms includes a plurality of quality factors, and the set of compressed digital images is generated based on the respective compression algorithms and quality factors.

13. The computer-implemented method of claim 10, wherein determining an amount of errors by comparison of a digital image to the uncompressed digital image comprises:
  by the one or more processors executing program instructions:
    determining a difference between the digital image and the compressed digital image to generate difference image data; and
    determining the amount of errors by at least one of:
      determining a number of pixels in the difference image data having a value indicative of an error, or
      determining a degree of error in one or more pixels of the difference image data.

14. The computer-implemented method of claim 10, wherein determining an amount of errors by comparison of a compressed digital image to the digital image comprises:
  by the one or more processors executing program instructions:
    identifying one or more pixels of the digital image having an intensity value satisfying a second threshold;
    for each pixel of the one or more pixels, determining a difference between the pixel of the digital image and the pixel of the compressed digital image to generate difference image data;
    determining the amount of errors by at least one of:
      determining a number of pixels in the difference image data having a value indicative of an error, or
      determining a degree of error in one or more pixels of the difference image data.

15. The computer-implemented method of claim 14, wherein each of the one or more pixels comprises a group of pixels, and wherein each group of pixels comprises at least one of: a 4×4 group of pixels, or a 6×6 group of pixels.

16. The computer-implemented method of claim 10, wherein determining an amount of errors by comparison of a compressed digital image to the digital image comprises:
  by the one or more processors executing program instructions:
    identifying one or more regions of the digital image having pixel intensity values satisfying a second threshold;
    for each pixel or group of pixels of the one or more regions, determining a difference between the pixel of the digital image and the pixel of the compressed digital image to generate difference image data; and
    determining the amount of errors by at least one of:
      determining a number of pixels in the difference image data having a value indicative of an error, or
      determining a degree of error in one or more pixels of the difference image data.

17. The computer-implemented method of claim 10 further comprising:
  by the one or more processors executing program instructions:

in response to determining that none of the compressed digital images of the set is associated with an amount of errors that satisfies the threshold, recompressing the uncompressed digital image using a lossless compression technique to generate a second compressed digital image; and storing the second compressed digital image in a data store.

18. The computer-implemented method of claim 10, wherein the highest compression level is a compression level that requires a least amount of storage space as compared to other compression levels of the plurality of compression levels, while also having the amount of errors that satisfies the threshold.

19. A non-transitory computer readable storage medium having software instructions embodied thereon, the software instructions executable by one or more processors to cause the one or more processors to:

compress a digital image using each of a plurality of compression algorithms, in parallel, to generate a set of compressed digital images that are compressed at a plurality of different compression levels;

for each of the compressed digital images of the set, determine a respective amount of errors based on comparison of the respective compressed digital images to the digital image; and determine a first compressed digital image of the set that is compressed at a highest compression level of the plurality of compression levels that also has an amount of errors that satisfies a threshold.

* * * * *